(12) United States Patent
Hosseini et al.

(10) Patent No.: US 11,998,186 B2
(45) Date of Patent: Jun. 4, 2024

(54) DEVICES AND METHODS FOR TISSUE REPAIR

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Ali Hosseini, Quincy, MA (US); Christopher David MacCready, Medfield, MA (US); Kendra O'Malley, Charlton, MA (US); Geoffrey Ian Karasic, Milton, MA (US); Zenan Qi, Attleboro, MA (US); Benjamin Michael Hall, Roslindale, MA (US); Chun Liu, Brookline, MA (US); Paul McGovern, Hanson, MA (US); Han Teik Yeoh, Albany, MA (US)

(73) Assignees: Smith & Nephew, Inc., Memphis, TN (US); Smith & Nephew Orthopaedics AG, Memphis, TN (US); Smith & Nephew Asia Pacific Pte. Limited, Memphis, TN (US)

( * ) Notice: Subject to any disclaimer, the term of this patent is extended or adjusted under 35 U.S.C. 154(b) by 0 days.

(21) Appl. No.: 18/556,790

(22) PCT Filed: Apr. 26, 2022

(86) PCT No.: PCT/US2022/026320
§ 371 (c)(1),
(2) Date: Oct. 23, 2023

(87) PCT Pub. No.: WO2022/232126
PCT Pub. Date: Nov. 3, 2022

(65) Prior Publication Data
US 2024/0081808 A1    Mar. 14, 2024

Related U.S. Application Data

(60) Provisional application No. 63/179,654, filed on Apr. 26, 2021, provisional application No. 63/278,644, filed on Nov. 12, 2021.

(51) Int. Cl.
*A61B 17/04* (2006.01)

(52) U.S. Cl.
CPC .. *A61B 17/0401* (2013.01); *A61B 2017/0404* (2013.01); *A61B 2017/0414* (2013.01)

(58) Field of Classification Search
CPC ............ A61B 17/0401; A61B 17/0487; A61B 2017/0404; A61B 2017/0414;
(Continued)

(56) References Cited

U.S. PATENT DOCUMENTS 1,618,398 A * 2/1927 Winslow ................. A44B 1/08
24/114.1
9,056,003 B2 * 6/2015 Demmer ............ A61B 17/0401
(Continued)

FOREIGN PATENT DOCUMENTS

WO  2007073563  6/2007
WO  2011003002  1/2011
WO  2020257432  12/2020

*Primary Examiner* — Dianne Dornbusch
(74) *Attorney, Agent, or Firm* — Norman F. Hainer, Jr.; Kate Ryland Tetzlaff

(57) ABSTRACT

Methods and devices for tissue fixation. A cortical button with a rib between two slotted openings. The rib increases the cortical button structural rigidity without increasing palpability. An adjustable loop construct with two discrete locking passages that provides manageable loop reduction and improved tissue coupling. The adjustable loop construct may be coupled to tissue via a passing construct. An assembly with a reduction bar, a button and an adjustable loop construct, the assembly provided assembled in a first configuration that disassembles to guide steps of tissue (Continued)

fixation. The reduction bar may be assembled to the reduction bar for reducing the adjustable loop construct.

18 Claims, 31 Drawing Sheets

(58) Field of Classification Search
CPC .... A61B 2017/0459; A61B 2017/0403; A61B 2017/0406; A61B 2017/0408
See application file for complete search history.

(56) References Cited

U.S. PATENT DOCUMENTS

| | | | |
|---|---|---|---|
| 2007/0162125 A1* | 7/2007 | LeBeau | A61F 2/0811 623/13.14 |
| 2007/0233241 A1* | 10/2007 | Graf | A61B 17/0401 623/13.14 |
| 2010/0125297 A1* | 5/2010 | Guederian | A61B 17/0401 606/232 |
| 2013/0172944 A1 | 7/2013 | Fritzinger et al. | |
| 2016/0038267 A1* | 2/2016 | Allen | A61F 2/0004 606/232 |
| 2022/0378412 A1* | 12/2022 | Chavan | A61B 17/0487 |

* cited by examiner

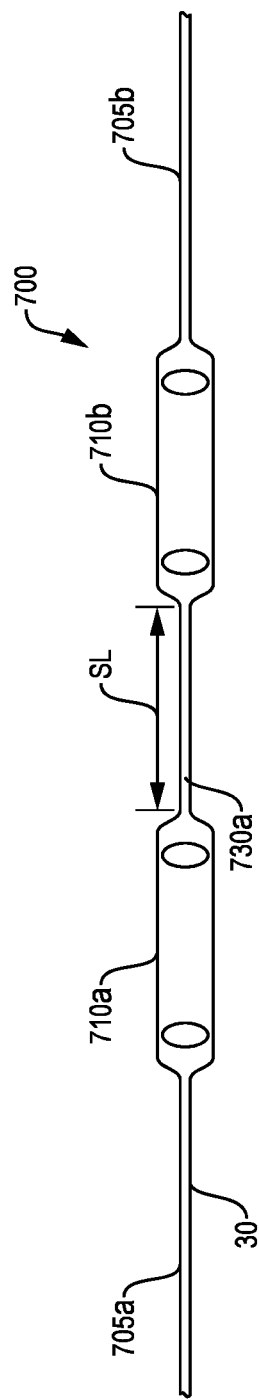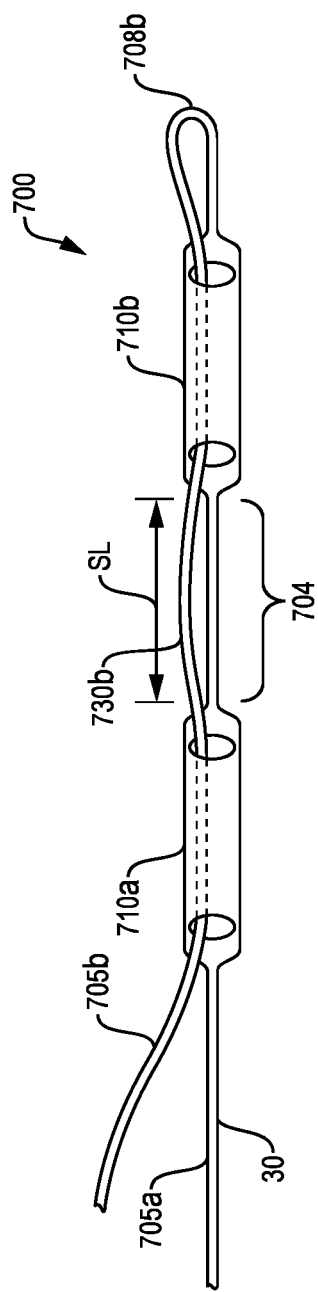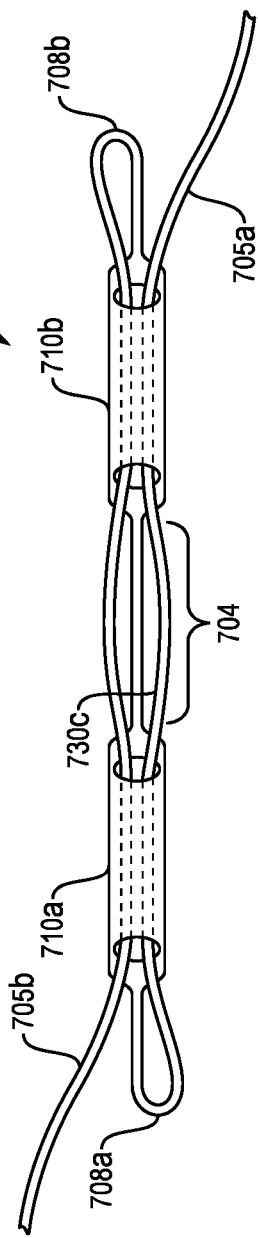

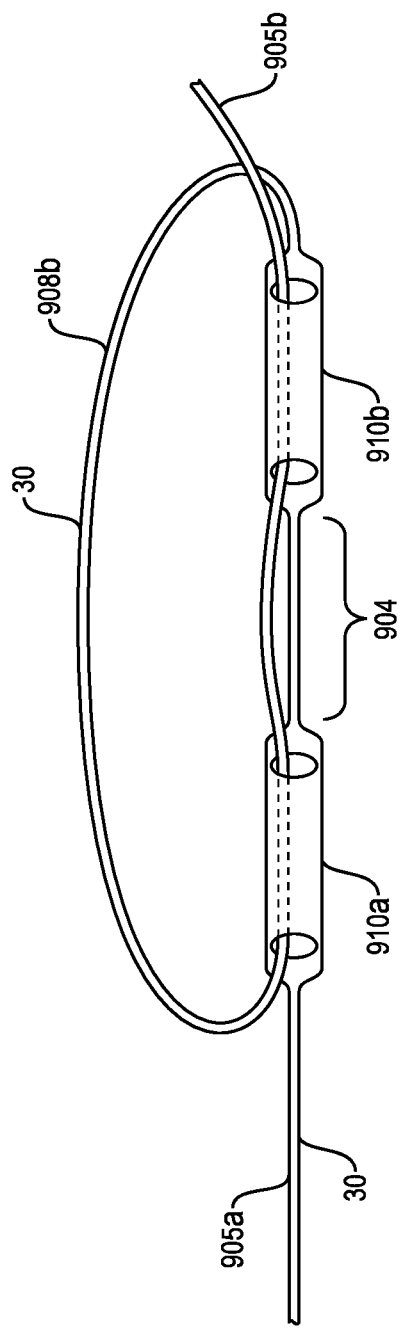
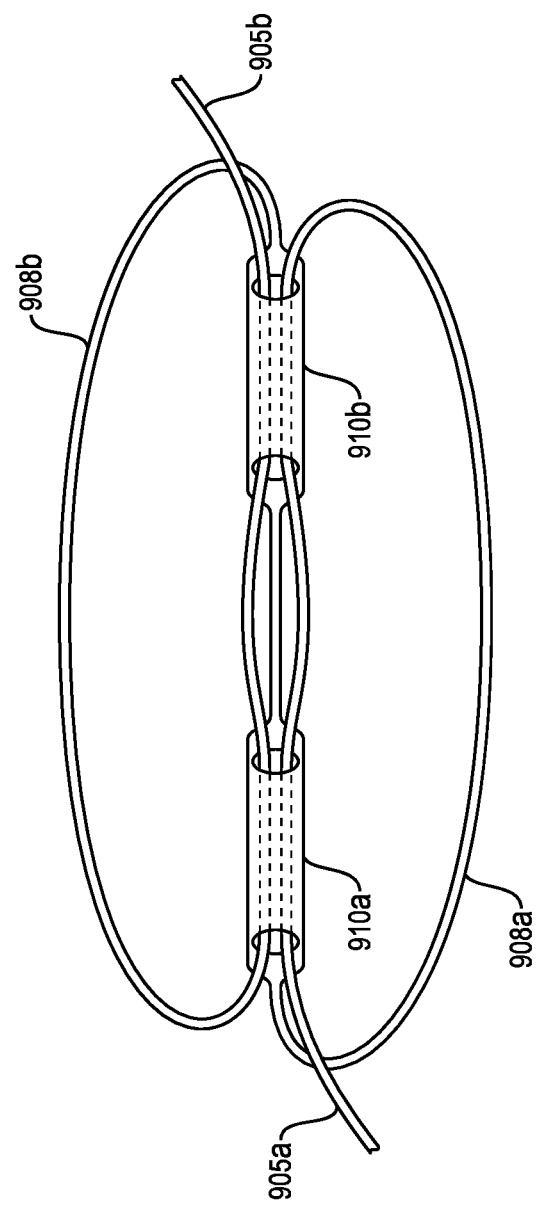

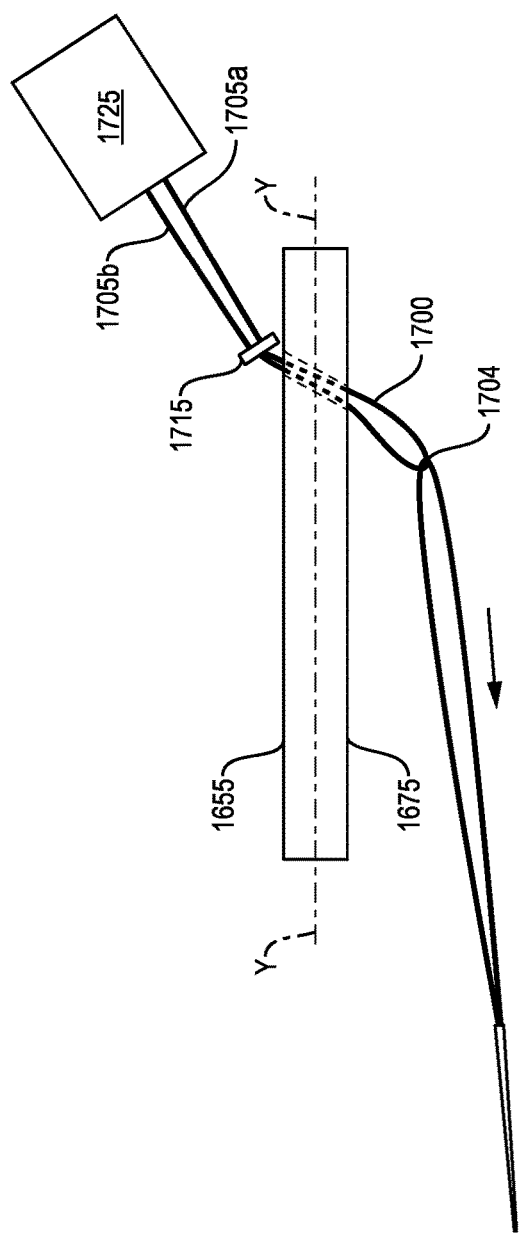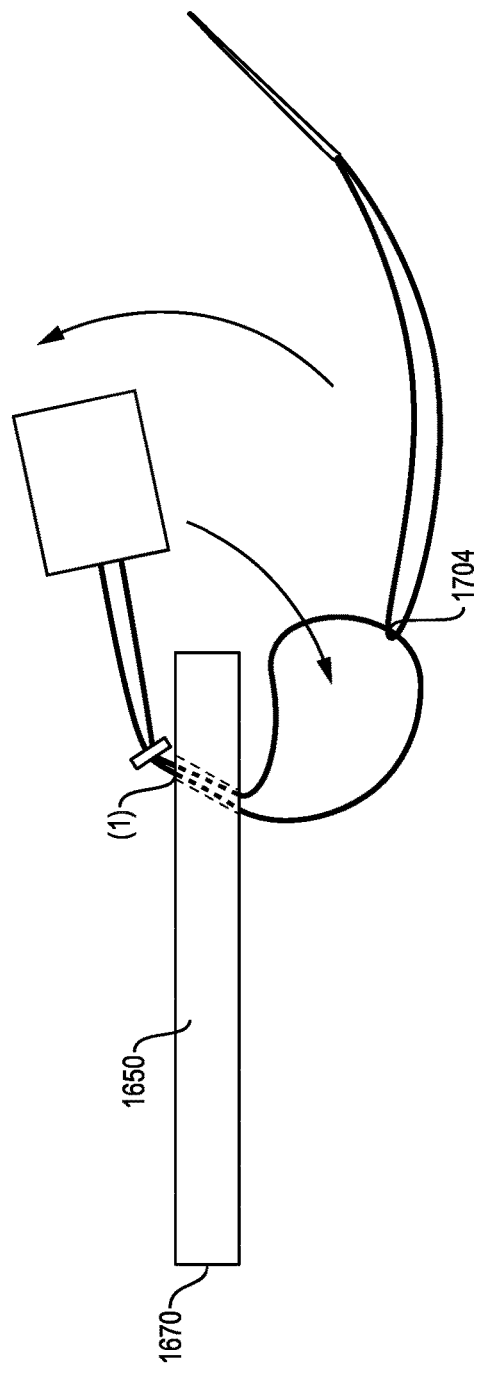
FIG. 17C
FIG. 17D

DEVICES AND METHODS FOR TISSUE REPAIR

CROSS-REFERENCE TO RELATED APPLICATIONS

This application is the U.S. national phase entry under 35 U.S.C. § 371 of International Application No. PCT/US2022/026320 titled "DEVICES AND METHODS FOR JOINT REPAIR," filed Apr. 26, 2022, which claims the benefit of U.S. Provisional App. No. 63/179,654 filed Apr. 26, 2021 titled "DEVICES AND METHODS FOR TISSUE REPAIR" and U.S. Provisional App. No. 63/278,644 filed Nov. 12, 2021 and titled "DEVICES AND METHODS FOR TISSUE REPAIR" all herein incorporated by reference in their entirety.

FIELD

The present disclosure relates to methods and devices for joint repair, including graft fixation in a surgical repair.

BACKGROUND

Native soft tissue (such as ligaments and tendons of a joint) that is damaged may generally be replaced or repaired arthroscopically. For some joint repairs, a tissue fixation system with an adjustable loop construct may be coupled to a graft (and/or also the native soft tissue) and inserted along a bone tunnel. The adjustable loop construct may then be adjusted or reduced to position the graft in a target location along the bone tunnel and fixed in place with a tissue anchor, such as a cortical button. Cortical buttons may define a thin body to lie flat on a bone external surface and limit palpability, while supporting the fixation loading on the adjustable construct. Related art cortical buttons may bend under this fixation loading. Related art adjustable loop constructs may loosen via loop slip or creep under this loading. Related art adjustable loop constructs may require extreme forces to reduce the adjustable loop construct and position the graft. Related art fixation systems may require complicated assembly and management to stage the steps of the procedure. Related art fixation systems may require high forces during coupling of the grafts to the system, potentially damaging the tissue and/or grafts, or the adjustable loop construct. There is therefore a need for an improved fixation system with associated methods that address the related art shortcomings.

SUMMARY

Described herein are various improvements in methods and devices for tissue fixation using a loop construct that may be adjustable and may be formed with a flexible strand. A flexible strand may comprise suture, suture tape, cable, wire or ribbon. The suture may comprise a hollow braided suture. Such improvements may include examples of tissue anchors that are partially assembled with an adjustable loop construct, and further assembled after the adjustable loop construct has been coupled to a tissue, a graft or a second tissue anchor. The tissue anchor is preferably configured to remain sufficiently rigid to withstand the tissue fixation loads. Such improvements may include an adjustable loop construct that affords loop reduction with accessible hand tension, while also providing a knotlessly locked configuration that withstands physiological cyclic loading. Such improvements may include an assembly including a reduction handle with a tissue anchor and an adjustable loop construct housed therein, the assembly arranged in such a way as to manage the steps of releasing the adjustable loop construct and anchor from the reduction handle for coupling the adjustable loop to the tissue, graft or second tissue anchor. The handle may also be configured to re-assemble with the adjustable loop construct for reducing the adjustable loop and positioning the tissue, graft or second tissue anchor. Such improvements may include a passing construct operatively coupled to the adjustable construct in an arrangement that reduces passing forces required to thread the adjustable loop strands through a tissue or graft. Such improvements may include a method of attaching soft tissue or graft to an adjustable loop construct that concomitantly forms a low-profile end of the soft tissue or graft and provides a secure attachment.

For example, a cortical button is disclosed herein that is an oblong body, having a length greater than a width. The oblong body extending from a first end to a second end and defining a longitudinal axis. The width extends from a first sidewall to a second sidewall, the first and second sidewalls extending between the first and second ends along and either side of the longitudinal axis. The body also includes a lower surface configured to engage an external bone surface. The body further includes a pair of slotted apertures extending through an entire thickness of the body for receiving a loop of flexible strand therethrough. The button includes a rib extending from the body lower surface and disposed between the pair of slotted apertures and coextensive along the longitudinal axis with the pair of slotted openings. The cortical button configured to be passed through a bone tunnel in an elongate orientation.

Some example button embodiments may also include a pair of enclosed apertures, adjacent the pair of slotted apertures. The rib may also be disposed between the pair of enclosed apertures and coextensive along the longitudinal axis with the pair of enclosed apertures. The cortical button may also include a first end aperture disposed between the pair of slotted apertures and first end, and a second end aperture disposed between the pair of enclosed apertures and second end. The first and second end apertures may be axially separated from the rib. The rib may be an oblong solid body and may have a longitudinal axis coincident with and parallel to the cortical button longitudinal axis. The pair of slotted apertures may each define medial surfaces that extend through the cortical button thickness and are continuous with outer lateral side surfaces of the rib. The pair of slotted apertures may each define a lateral opening through one of the first or second sidewalls, and wherein the rib is configured to compensate for a reduced structural integrity of the cortical button, the reduced structural integrity a result of the lateral openings. The rib may extend perpendicularly from the lower surface, less than 2 mm from the cortical button oblong body. The rib may extend from the lower surface defining a tib thickness that is less than the body thickness.

Another example cortical button is disclosed that is an oblong body, having a length greater than a width, the length extending from a first end to a second end with a longitudinal axis extending therebetween. The width extends from a first sidewall to a second sidewall, the first and second sidewalls extending between the first and second ends along and either side of the longitudinal axis. The body also includes a lower surface configured to engage an external bone surface. The body also includes a pair of slotted apertures extending through an entire thickness of the body for receiving a loop of a flexible strand therethrough. The button anchor includes a rib extending from the lower surface and disposed between the pair of slotted apertures and coextensive along the longitudinal axis with the pair of slotted openings. The body width defines a minimum diameter of a bone tunnel through which the cortical button may be passed, the rib configured to increase the structural integrity of the cortical button while preserving the minimum diameter.

In some example embodiments, the pair of slotted apertures each define a lateral opening through one of the first or second sidewalls, and the rib is configured to increase the structural integrity and compensate for a loss of structural integrity due to the lateral openings. The body may also include a pair of enclosed apertures, adjacent the pair of slotted apertures, the rib disposed between the pair of enclosed apertures and coextensive along the longitudinal axis with the pair of enclosed apertures. The pair of slotted apertures may each define a lateral opening through one of the first or second sidewalls, and wherein the rib is coextensive along the longitudinal axis with the lateral openings. The button body may also include a first end aperture and a second end aperture, both axially separated from the rib. The rib may be an oblong solid body. The rib may be an oblong body having a longitudinal axis coincident with and parallel to the cortical button longitudinal axis. The pair of slotted apertures may each define medial surfaces that extend through the cortical button thickness and are continuous with outer lateral side surfaces of the rib. The rib may extend perpendicularly from the lower surface, less than 2 mm from the cortical button body. The rib may extend from the lower surface a distance that is less than a thickness of the body.

An adjustable tissue repair system is also disclosed including a tissue anchor with a plurality of apertures therethrough. The system also includes an adjustable loop construct formed from a flexible strand and coupled to the tissue anchor via the plurality of apertures. The adjustable loop construct includes a first adjustable eyesplice loop extending through a first pair of apertures of the plurality of apertures. The adjustable loop construct also includes a second adjustable eyesplice loop configured to couple to a second pair of apertures of the plurality of apertures. The adjustable loop construct also includes a saddle portion extending between the first and second adjustable eyesplice loops and disposed at an opposite end of the adjustable loop construct to the tissue anchor. The adjustable loop construct also includes a first and second limb, the first limb tensionable for shortening the first adjustable eyesplice loop and the second limb tensionable for shortening the second adjustable eyesplice loop.

In some example embodiments, the first and second eyesplice loops each include a locking passage, and wherein each locking passage includes two lengths of the flexible strand therethrough. The saddle portion may define three lengths of the flexible strand extending therealong, between locking passages. One of the three lengths of these flexible strands may be a static strand, such that while adjusting the adjustable loop construct, the static strand does not slide. Static strand defines a fixed or non-adjustable length portion of the adjustable loop construct. The fixed length may be between 0.10-0.5 inches. The fixed length during ACL repair may be about 0.25 inches. The tissue repair system may also include a passing construct including a threading member and a flexible loop, the flexible loop coupled to the saddle portion of the adjustable loop construct. The saddle portion may include three lengths of the flexible strand and wherein the flexible loop may be threaded between the three lengths in a complex loop, to limit sliding of the flexible loop along the adjustable loop construct. The flexible loop may be threaded between the three lengths of flexible strand of the saddle portion to stagger insertion of the three lengths through a graft. The flexible loop may be coupled to the saddle portion and form a figure-of-eight loop around the three lengths of the flexible strand. The figure-of-eight loop may include a first loop that loops around a static length of the three lengths of the flexible strand, and a second loop that loops around two dynamic lengths of the three lengths of flexible strand. The plurality of openings through the tissue anchor may include a pair of lateral slotted openings configured to selectively receive the second adjustable eyesplice loop therethrough. The saddle portion may couple directly to graft or tissue. The first and second eyesplice loops may each extend from a first and second locking passage respectively, and the first eyesplice loop and first limb both extend from a first end of the first locking passage and the second eyesplice loop and second limb both extend from a first end of the second locking passage.

Another adjustable tissue repair system embodiment is disclosed including a tissue anchor with a plurality of apertures therethrough and an adjustable loop construct formed from a flexible strand and coupled to the tissue anchor via the plurality of apertures. The adjustable loop construct may include a first adjustable eyesplice loop extending from a first locking passage, the first adjustable eyesplice loop extending through a first pair of apertures of the plurality of apertures. The adjustable loop construct may include a second adjustable eyesplice loop extending from a second locking passage, the second adjustable eyesplice loop configured to couple to a second pair of apertures of the plurality of apertures. The adjustable loop construct may include a saddle portion extending between the first and second adjustable eyesplice loops, disposed at an opposite end of the adjustable loop construct to the tissue anchor. The adjustable loop construct may include a first and second limb, the first limb tensionable for shortening the first adjustable eyesplice loop and the second limb tensionable for shortening the second adjustable eyesplice loop. The system may include a passing construct including a threading member coupled to a flexible loop, the flexible loop coupled to the saddle portion.

In some example embodiments, the saddle portion includes three lengths of the flexible strand. One of the three lengths of the flexible strand may be a static length of the adjustable loop construct extending between and continuous with the first and second locking passage. The static length may be between 0.10-0.5 inches long. The flexible loop of the passing construct may be threaded between the three lengths of flexible strand of the saddle portion to stagger insertion of the three lengths through a graft. The flexible loop may be coupled to the saddle portion and form a figure-of-eight loop around the three lengths. The figure-of-eight loop may define a first loop that loops around a static length of the three lengths of flexible strand, and a second loop that loops around two dynamic lengths of the three lengths of flexible strand. The first eyesplice loop and the first limb may both extend from a first end of the first locking passage and the second eyesplice loop and the second limb may both extend from a first end of the second locking passage.

An example method of coupling an adjustable tissue repair construct to a graft is also disclosed, the method including obtaining an adjustable tissue repair construct that includes a button, an adjustable loop construct and a passing construct. The button includes a plurality of openings therethrough. The adjustable loop construct is formed with a flexible strand and coupled to the button via the plurality of openings at a first end of the adjustable loop construct. The passing construct includes a flexible strand loop and a threading member, the flexible strand loop separately formed from the adjustable loop construct and coupled to a second end of the adjustable loop construct, at the opposing end to the first end. The method includes forming a stitched region in the graft by first passing the passing construct through the graft in a first direction toward a clamped end of the graft to attach the adjustable loop construct to the graft and then passing the passing construct though the graft in an opposite direction towards a free end of the graft to attach the flexible strand loop to the graft.

In some example methods, advancing the passing construct in the first direction, further comprises drawing the adjustable loop construct through and around the graft at a location spaced away from both the clamped end and free end. The method may include passing the passing construct through the graft adjacent the adjustable loop construct that is threaded around the graft, and thereby locking the adjustable loop construct in place along the graft. Passing the passing construct in the opposite direction may wrap the flexible strand loop around the graft and also over and around the adjustable loop construct. Passing the passing construct in the opposite direction may form at least two whipstitches along and through the graft.

The method may also include passing the passing construct in the opposite direction up to a free end edge of the graft, tying a knot in the flexible strand loop at the free end edge, removing the threading member from the flexible strand loop, leaving a remaining length of flexible strand loop; and drawing the free end of the graft through and along a prepared bone tunnel via the remaining length.

The flexible strand loop may form a figure-of-eight loop, a first loop of the figure-of-eight loop looped around a first strand of a plurality of strands of the adjustable loop construct at the second end, and a second loop of the figure-of-eight loop looped around a second strand of a plurality strands and wherein passing the passing construct in a first direction first passes the second loop and therefore the second strand through the graft, and then passes the first loop and therefore the first strand through the graft. Passing the passing construct in the second direction may leave the first loop of the figure-of-eight loop on a first side of the graft and passes the second loop of the figure-of-eight loop through the graft.

Another example method of coupling a suspensory fixation system to a graft is disclosed, the suspensory fixation system including an adjustable loop construct and a passing construct linked thereto. The method includes forming a first stitched region along the graft by inserting the passing construct through the graft and advancing the passing construct in a first direction toward a clamped end of the graft to stitch the adjustable loop construct through and along the graft. The method also includes forming a second stitched region by inserting the passing construct through the graft and advancing the passing construct in second direction toward a free end of the graft to stitch a flexible loop of the passing construct through and along the graft, the second stitched region overlapping the first stitched region.

In some of these example methods, advancing the passing construct in the first direction begins along a length of the graft spaced away from the free end. Forming the first stitched region may begin at a location along the graft that is about 2 cm from the free end. Inserting the passing construct through the graft and advancing the passing construct in the first direction may include inserting the passing construct a first time to stitch the adjustable loop construct through the graft followed by inserting the passing construct a second time through the graft to secure the adjustable loop construct in place along the graft. Advancing the passing construct in the second direction may include inserting the passing construct a third time and a fourth time through the graft at axially spaced locations, to form a plurality of stitches through the graft with the flexible loop. Passing the passing construct, a third time, may place the flexible loop over the adjustable loop construct. of claim 54 wherein inserting the passing construct through the graft a first, second, third and fourth time comprises passing the needle from a top external surface of the graft to a bottom external surface of the graft. After forming the first and second stitched region, the method may include tensioning the flexible loop to form the graft free end into a tapered cylinder. The method may also include drawing the free end into a prepared bone tunnel by drawing the flexible loop through the prepared bone tunnel first and then the graft free end.

In some example methods, the flexible loop may form a complex loop, a first loop of the complex loop looped around a first strand of a plurality of strands of the adjustable loop construct, and a second loop of the complex loop looped around a second strand of the plurality of strands and wherein forming the first stitched region may insert the second loop through the graft first, followed by the first loop, and thereby stagger the insertion of the plurality of strands to reduce a force required to form the first stitched region. Forming the second stitched region may leave the first loop of the complex loop on a top side of the graft and may pass the second loop of the complex loop through the graft. The flexible loop may include a complex loop including a first and second loop, each loop looped around different strands of the adjustable loop construct and advancing the passing construct in second direction may advance only one of the first or second loops.

A reduction bar is also disclosed herein, for managing an adjustable loop construct with a passing construct and a button attached thereto, the reduction bar including a plurality of channels, spools, recesses, and slots therethrough. The reduction bar houses the passing construct, the adjustable loop construct, and the button in a first configuration within the plurality of channels, slots, and spools, in an arrangement that stages the release of the assembled components. The passing construct may be release first, followed by the adjustable loop construct and then the button from the reduction bar to couple the adjustable loop construct to a tissue, graft, or tissue anchor. Once disassembled, the reduction bar may then assemble again to the adjustable loop construct in a second configuration that is different than the first configuration. In this second configuration the reduction bar may be used to reduce a loop of the adjustable loop construct and draw the tissue, graft, or tissue anchor towards the button upon tension being applied via the reduction bar to the adjustable loop construct.

In some example embodiments the reduction bar includes a slot of the plurality of slots that extends along a longitudinal axis of the reduction bar, the slot continuous with a recess, the slot configured to retain a threading member of the passing construct and the recess configured to allow access to an end of the threading member to remove the threading member from the reduction bar. In the second configuration, a first looped limb of the adjustable loop construct may encircle a segment of a first spool of the reduction bar, the segment defined by a notch through the first spool. In the second configuration rotating the reduction bar around a reduction bar longitudinal axis may first form a fold along the first looped limb to limit slipping of the first looped limb around the first spool. The reduction bar may house the button so as to expose two slotted apertures of the button. The reduction bar may house a first portion of the adjustable loop construct around a first spool of the plurality of spools and a second portion of the adjustable loop construct around a second spool of the plurality of spools.

Another example embodiment of a reduction handle is disclosed that houses and manages an adjustable loop construct. The adjustable loop construct includes a first end assembled to a cortical button and a second end coupled to a threading element for coupling the second end to a tissue, a graft, or a tissue anchor. The reduction handle defines a longitudinal axis and opposed lateral ends and also includes a slot at one of the lateral ends for retaining the cortical button. The slot may also orient a slotted opening of the cortical button for selectively receiving the adjustable loop second end therethrough. The reduction handle may also include a means of housing the threading element and a means directly adjacent thereto for accessing and selectively removing the threading element from the reduction handle. The reduction handle may also include a first and a second spool extending around an outer surface of the handle, a first and a second loop of the adjustable loop construct receivable in the first spool and second spool respectively.

In some example embodiments the means of housing the threading element includes a plurality of circumferential ribs defining a channel on an external surface of the reduction handle, and wherein a cavity in the handle at an end of the channel defines the means of accessing and selectively removing the threading element. The first and second spools may each define an outermost channel defining a first path, each outermost channel intersected by a corresponding notch defining a second path around a segment of the first path of each spool. The first loop of the adjustable loop construct may be receivable along the notch of the first spool so as to place the first loop along the second path around the first spool. The second loop of the adjustable loop construct may be receivable along the notch of the second spool to place the second loop along the second path around the second spool. The second path around each spool may be configured to form a fold in each loop of the first and second loop and limit spinning of the first and second loop while rotating the handle about its longitudinal axis.

A method of repairing a tissue with a reduction bar is also disclosed, the reduction bar preassembled to an adjustable loop construct, a cortical button, and a threading element. The method may include removing the adjustable loop construct and the threading element from the reduction bar and coupling the adjustable loop construct to a tissue, a graft or a tissue anchor. The method may include coupling a first and a second loop end of the adjustable loop construct to the reduction bar after it has been removed. Tension may then be applied on the first and second loop end via the reduction bar to reduce the adjustable loop construct and draw the tissue, graft, or tissue anchor towards the cortical button.

In some example methods, removing the adjustable loop construct and the threading element may include removing the threading element from a channel of the reduction bar, followed by unspooling a first portion of the adjustable loop construct from a first spool of the reduction bar. Coupling the adjustable loop construct may include inserting the adjustable loop construct through the tissue, graft, or tissue anchor with the threading member. Removing the adjustable loop construct and the threading element from the reduction bar may occur while retaining the button housed within the reduction handle. Coupling may also include coupled a free looped end of the adjustable loop construct to the cortical button after coupling the adjustable loop construct to a tissue, graft, or tissue anchor. Coupling the free looped end may include inserting the threading member through an aperture of the button while the button is housed within the reduction bar, with an aperture external to the reduction bar.

Coupling the first and a second looped ends may include inserting the first looped end along a first notch of the reduction bar to place the first looped end around a segment of a first spool on the reduction bar and inserting the second looped end along a second notch of the reduction bar to place the second looped end around a segment of a second spool of the reduction bar. The method may also include rotating the reduction bar around a longitudinal axis to wrap the first and second looped ends around an outermost surface of the first and second spool respectively and thereby reduce a length of the first and second looped end. Rotating the reduction bar and applying tension on the first and second looped ends may be performed sequentially and repeatedly. The method may include removing the button after coupling the adjustable loop construct to a tissue, graft or tissue anchor and before coupling a first and a second looped end to the reduction bar.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein:

FIGS. 8A-8C illustrate a method of forming the adjustable loop construct in FIG. 7 in accordance with this disclosure;

FIGS. 9B-9C formation of the adjustable loop construct with two locking passages in accordance with this disclosure;

FIGS. 17A-17J illustrates a method of coupling an adjustable loop construct and passing loop construct to a graft, in accordance with this disclosure.

DETAILED DESCRIPTION

Figure 1A:
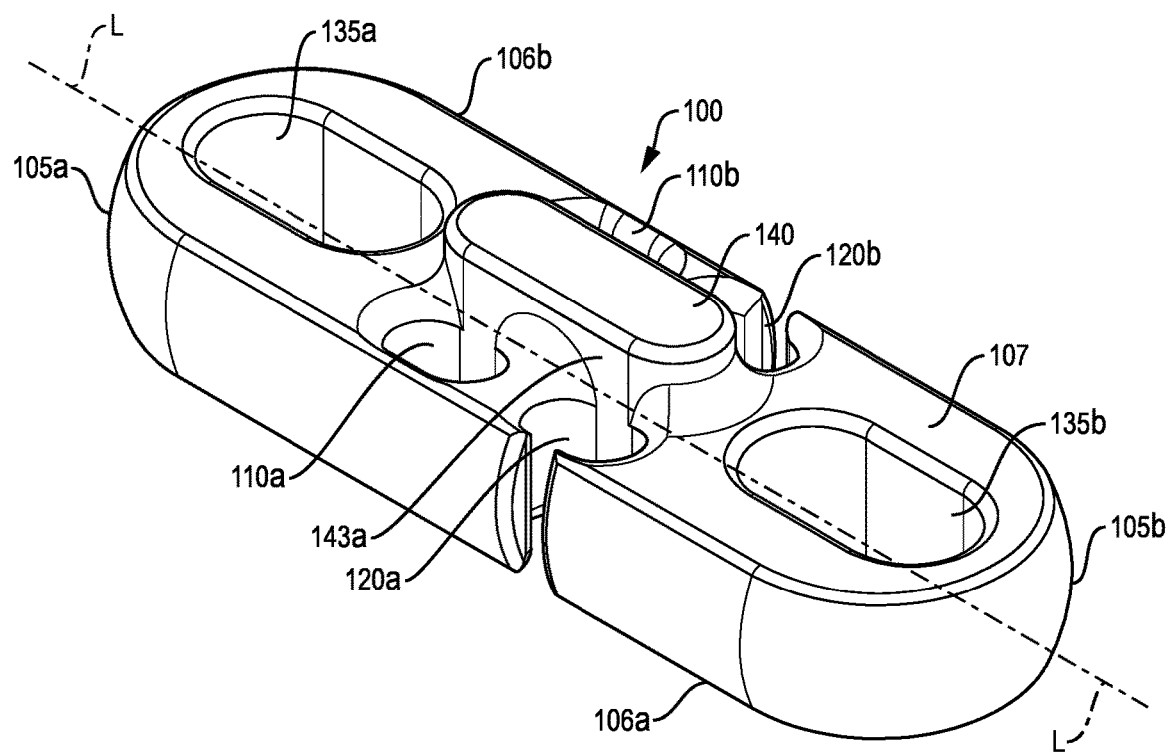
FIG. 1A illustrates a perspective view of a ribbed cortical button, in accordance with this disclosure.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used to represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts. Use of the terms "upper," "lower," "upwards," and the like is intended only to help in the clear description of the present disclosure and are not intended to limit the structure, positioning and/or operation of the disclosure in any manner.

Some of the constructs disclosed herein incorporate "locking passages". These may sometimes be referred to in the art as splices, eyesplices, cradles, suture locking regions, cinches, finger cinches, finger traps, longitudinal passages or dilated regions. They are defined by a length of a braided flexible strand with a hollow core that may receive an elongate strand therethrough. The elongate strand may be a different portion of the flexible strand, or another separate flexible strand and may extend along a path that extends from outside the braided flexible strand (and outside the locking passage) then between the braids to enter the hollow core (lumen) and then exit through the braided wall a distance along the braided flexible strand later. Multiple lengths of flexible strands may extend along and through the hollow core at spaced apart locations, thereby defining multiple locking passages. Multiple lengths of an elongate strand may extend along and through the hollow core at the same location. The braided flexible strand may be dilated first to form a dilated or laterally extended length before receiving the elongate member therein. The locking passage is configured such that tension on the braided hollow flexible strand contracts the radius thereof and thereby locks or cinches around the elongate strand extending therein, locking the elongate strand in place. This defines a "locking passage". The flexible strand may be a suture, suture tape, ribbon, or flexible tubular cable.

Cortical Button Embodiments

FIG. 1A illustrates a perspective view of a cortical button 100 (hereinafter "button 100"), in accordance with example embodiments. Button 100 operatively couples to a flexible strand 30 (shown in FIGS. 3A-3H) via a plurality of openings forming passages through the button 100. Flexible strand 30 may be a suture, tape, wire or cable and may be formed in an adjustable loop construct, disclosed in more detail hereinafter. Button 100 and flexible strand 30 may couple to a graft and suspend the graft along a bone tunnel, for repair of an ACL of a patient's knee for example. In other example joint repairs, button 100 and flexible strand 30 may couple to another tissue anchor such as a second button, or a soft anchor or other tissue anchors known in the art. When coupled to another tissue anchor, button 100 and flexible strand 30 may couple a first bone to a second bone, or a first bone segment to a second bone segment, wherein the segments may be parts of the same bone. For example, button 100 may form a portion of a repair construct for AC joint or ankle syndesmosis repair.

Button 100 may define a passing button; in that it is generally an oblong body with a width that is smaller in dimension than a length thereof. Passing buttons may be oriented in a passing orientation to pass through a bone tunnel, the bone tunnel approximating the anchor width, allowing the bone tunnel to be kept to a minimal opening size. Once through the bone tunnel, flipping the button 100 to a deployed configuration (shown in FIG. 3G) prevents retrograde motion of the button 100 into the tunnel, as the button length is greater than the bone tunnel opening size. In the deployed configuration button 100 engages the cortical bone outer surface. Button 100 may be a flat, oblong unibody with rounded edges. Button 100 is preferably thin to limit palpability above the cortical bone surface.

Button 100 may include a plurality of apertures therethrough, each aperture sized to receive a flexible strand 30 therethrough and couple the flexible strand 30 to the button. Flexible strand 30 may be at least partially formed in a plurality of loops, in the form of an adjustable loop construct (discussed more in FIGS. 3A-3H), and the plurality of apertures may couple the adjustable loop construct to the button 100. The plurality of apertures may be sized to allow the flexible strand 30 to slide.

More specifically, button 100 may include a pair of apertures 110a, 110b that may define 360 degree (°) bounded holes. Apertures 110a, 110b may be disposed directly opposite each other on opposing sides of the button longitudinal axis L-L. Apertures 110a, 110b may define oblong or oval shaped openings having a length along the longitudinal axis L-L greater than a corresponding width. Apertures 110a, 110b may be sized and spaced relative to each other to slidingly receive a first loop of an adjustable loop construct, formed of flexible strand 30. First loop may be provided pre-assembled to the button 100, and therefore may be referred to as the assembled loop. Button 100 may also include a pair of slotted apertures 120a, 120b that have each have a lateral opening (121a, 121b), the lateral openings 121a, 121b for receiving a second loop of the adjustable loop construct therethrough to assemble the second loop to the button 100 during the procedure. As such slotted apertures 120a, 120b may be provided separated from the second loop, and the second loop may be assembled to the button 100, entering via lateral openings 121a, 121b during the surgical procedure. Second loop may therefore be referred to as a free loop. Slotted apertures 120a, 120b may define oblong or oval shaped openings similar to apertures 110a, 110b having a length along the longitudinal axis longer than a width. Slotted apertures 120a, 120b may be disposed directly opposite each other on opposing sides of the button longitudinal axis L-L. Slotted apertures 120a, 120b and apertures 110a, 110b may have the same opening size and shape, with the exception that slotted apertures 120a, 120b includes lateral openings 121a, 121b.

Button 100 defines an elongate body having opposed rounded ends 105a, 105b and lateral sides 106a, 106b. Apertures 110a, 110b, 120a, 120b may be arranged towards a central portion 138 of the button 100 spaced away from both ends 105a, 105b. Button also includes another pair of apertures 135a, 135b. Aperture 135a is disposed between the central portion 138 and lateral end 105a. Aperture 135b is disposed between the central portion 138 and lateral end 105b. Apertures 135a, 135b may be larger in opening size relative to apertures 110a, 110b, 120a, 120b and may define oblong apertures, as defined herein.

Button 100 also defines an upper surface 108 and lower surface 107, that may both be smooth and planar. Upper and lower surface 108, 107 may define planar surfaces that are parallel to each other. Button lower surface 107 is configured to engage an external portion of a bone. In some embodiments button lower surface 107 may be contoured to match an external surface of the targeted bone surface. Buttons with apertures and slotted apertures and example adjustable loop constructs are disclosed in commonly owned PCT patent application number PCT/US20/038401 filed Jun. 18, 2020, titled "METHODS AND DEVICES FOR TISSUE GRAFT FIXATION" commonly owned and herein incorporated by reference in its entirety.

As discussed herein, surgical fixation systems with cortical buttons may operate to couple to and suspend a graft within and along a bone tunnel of an articulating joint, and therefore experience load during use. Having a button that assembles to an adjustable loop construct during the procedure as opposed to providing the button completely preassembled, may provide improved methods for coupling the fixation system to a graft. However, the lateral openings 121a, 121b that accommodate inter-procedural assembly may reduce structural integrity of button, relative to apertures that enclosed (360 degree bounded holes). This may be compensated for by increasing an overall thickness (T) of the button body, however increasing thickness may increase palpability or local tissue irritation, and therefore is less preferable. Button 100 therefore includes an oblong rib 140 extending from lower surface 107, configured to increase button rigidity and compensate for a button configured to receive a free loop of a flexible strand 30 during the procedure. Rib 140 is sized to fit within and extend along a bone tunnel while surface 107 engages the external cortical surface of the bone surrounding the bone tunnel. Rib 140 is configured to increase the button structural rigidity under functional loading without increasing the thickness (T) of the button that stands proud of the bone external surface. Rib 140 may be configured to compensate for this reduced structural integrity, while maintaining a minimal thickness T.

Rib 140 may also help to center the elongate button 100 and hinder the button from moving relative to the bone tunnel axis. Rib 140 therefore has a length that extends substantially across an opening size (diameter) of a bone tunnel and also substantially axially into and along the bone tunnel, while still fitting along the limited bone tunnel diameter; the limited bone tunnel diameter defined by a width of the button body, as shown in FIG. 1C. Stated in another way, with reference to FIG. 1C, the cross section of the button including the button body and rib has an outer peripheral boundary that lies within a diameter (øD) defined by a width of the button body. For example, for a tunnel opening diameter of 4.5 mm, button body width may be between 4.2 mm, the rib length is preferably less than 4.0 mm and greater than 2.0 mm. More specifically in this example, rib length may be 3.5 mm in length $L_R$ and approximately 2 mm in width. Rib 140 may extend at least 1.5 mm ($T_R$) from a button body lower surface. Rib 140 may be a solid cross section or hollow, as its purpose is to maintain the button location relative to the bone tunnel, more so than any structural rigidity. As such, example rib could be an annular oblong ring, or a plurality of smaller posts at spaced apart locations configured to lie within the target bone tunnel and maintain a location of the button relative to the bone tunnel axis.

Figure 1B:
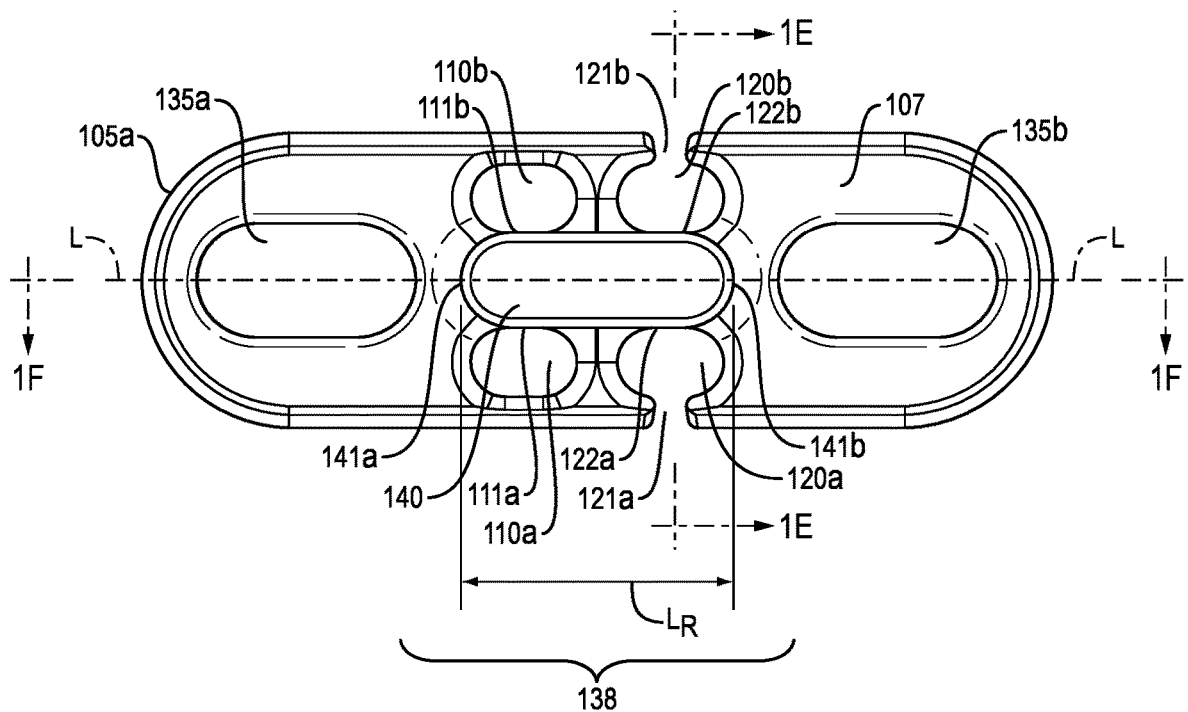
FIG. 1B illustrates a bottom view of the ribbed cortical button, in accordance with this disclosure.
Figure 1C:
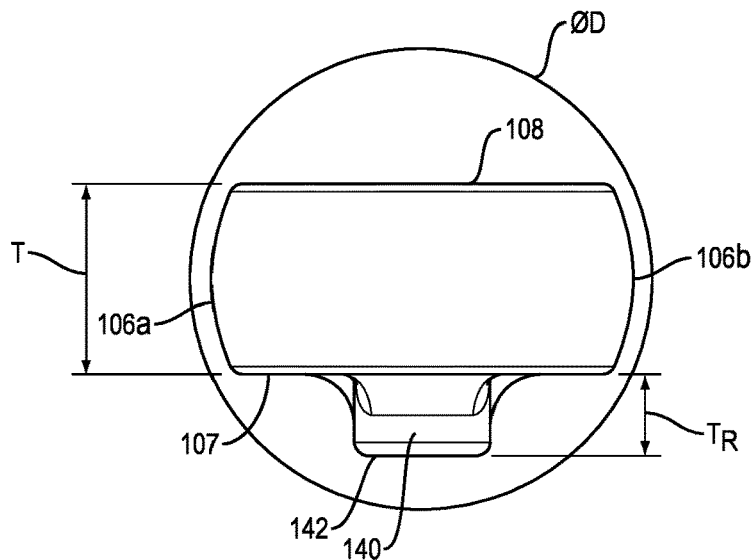
FIG. 1C illustrates an end view of the ribbed cortical button, in accordance with this disclosure.
Figure 1D:
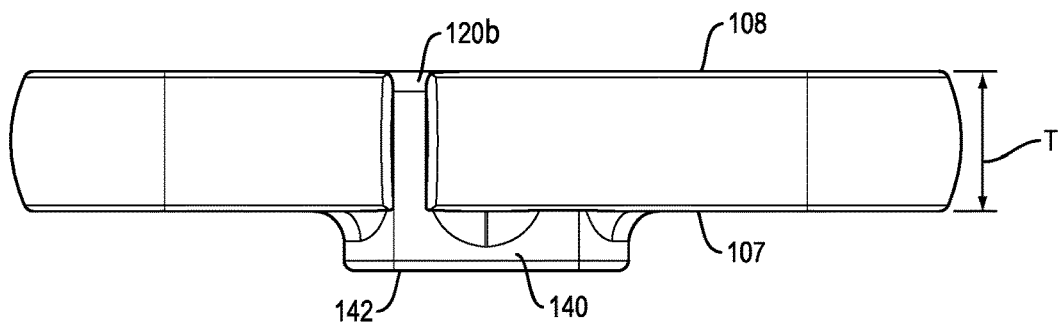
FIG. 1D illustrates a side view of the ribbed cortical button, in accordance with this disclosure.

Seen perhaps best in FIG. 1B, rib 140 is disposed along the longitudinal axis L-L and in-between apertures 110a, 110b, 120a, 120b. Rib 140 is also disposed along the central portion 138 of the button 100. Rib 140 may be equally spaced from ends 105a, 105b. Rib 140 has a length $L_R$ that extends along the longitudinal axis L-L, with apertures 135a, 135b disposed, adjacent ends of rib 140. Rib 140 and apertures 135a, 135b may lie along the longitudinal axis L-L. Longitudinal axis may bifurcate the rib 140 and apertures 135a, 135b. Rib 140 is axially spaced from both apertures 135a, 135b. Rib 140 may have a width that is narrower than a corresponding width of apertures 135a, 135b. Rib length $L_R$ may approximate a bone tunnel diameter thereby fitting within the bone tunnel and allowing surface 107 to engage bone outer surface. Rib length $L_R$ may axially overlap at least a portion of both apertures 110a, 110b, and 120a, 120b. Rib 140 may preferably axially overlap lateral openings 121a and 121b. Rib 140 may axially overlap entire lateral openings 121a, 121b. Stated in another way, rib 140 defines an elongate body having first and second ends 141a, 141b, where second end 141b is disposed axially closer to button end 105b than both of the lateral openings 121a, 121b in their entirety. Second end 141b may also be disposed axially closer to button end 105b than both of the slotted apertures 120a, 120b, in their entirety. Rib 140 is configured to add structural reinforcement to the button 100, allowing the thickness T that protrudes above the bone surface to remain low in profile. Rib 140 may compensate for a reduced structural integrity, the reduced structural integrity due to the lateral openings 121a, 121b.

Figure 1E:
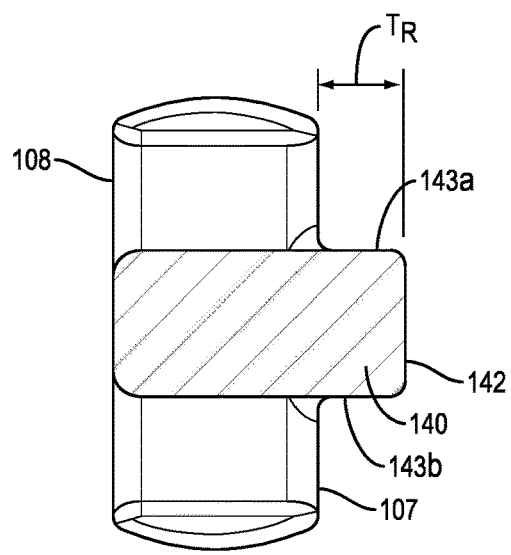
FIG. 1E illustrates a cross section view of the ribbed cortical button through B-B (shown in FIG. 1B), in accordance with this disclosure.
Figure 1F:
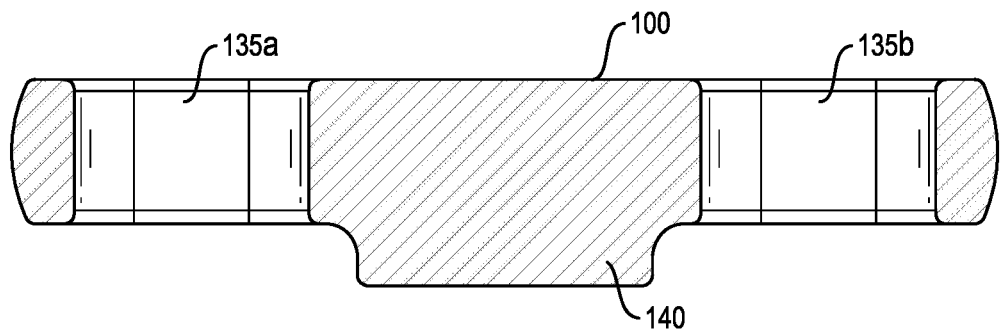
FIG. 1F illustrates a cross section view of the ribbed cortical button through A-A (shown in FIG. 1B), in accordance with this disclosure.
Figure 1G:
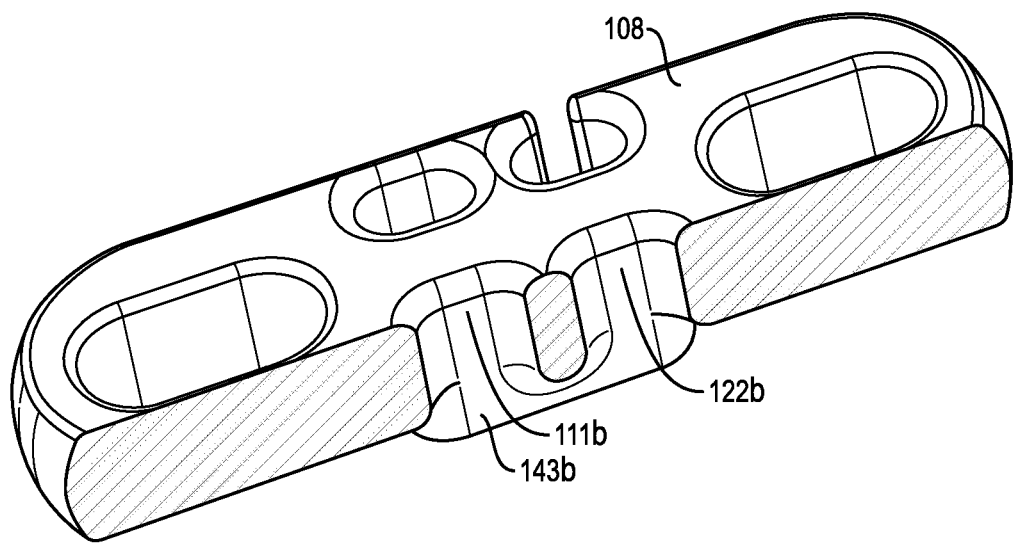
FIG. 1G illustrates an offset cross section view (from the longitudinal axis) of the ribbed cortical button through C-C (shown in FIG. 1B), in accordance with this disclosure.

Best seen in FIG. 1A and FIG. 1G, rib 140 may define planar side surfaces 143a, 143b, that may be parallel to longitudinal axis L-L and to each other. Planar surfaces 143a, 143b may be coincident with medial edge surfaces 111a, 111b, 122a, 122b of slotted apertures 120a, 120b and apertures 110a, 110b. Planar surfaces 143a, 143b may be continuous with medial edge surfaces 111a, 111b of apertures 110a, 110b and medial edge surfaces 122a, 122b of slotted apertures 120a, 120b respectively. Medial edge surfaces 111a, 122a and planar surface 143a may all lie on a single planar vertical surface. Medial edge surfaces 111b, 122b and planar surface 143b may all lie on a single planar vertical surface.

Illustrated in FIG. 1E and FIG. 1F, rib 140 extends from lower surface 107 and may define a solid cross section, free of voids. Rib 140 may extend perpendicularly from button lower surface 107, defining a rib thickness $T_R$. The combined thickness of button "T" and rib "$T_R$" may be equal to or less than a width of button 100, so as to fit along bone tunnel (FIG. 1C). FIG. 1C illustrates an example bone tunnel having diameter "øD", relative to the button 100 that is in the elongate (passing) orientation. Rib 140 may extend 1-3 mm ($T_R$) from lower surface 107. Rib 140 may define a lower surface 142 that is planar, the lower surface 142 parallel with lower surface 107. In other embodiments, lower surface 142 may be curved.

In other embodiments cortical button may include four apertures that all define 360 degree bounded holes, in similar locations to apertures 110a, 110, 120a, 120b. These example cortical buttons may be oblong, may be passing buttons as defined herein and may also include an oblong rib, similar to rib 140. While compensation for slots such as slots 121a, 121b is not required in this embodiment, inventors have found that these buttons may also benefit from the centering aspect provided by the rib 140.

Figure 2A:
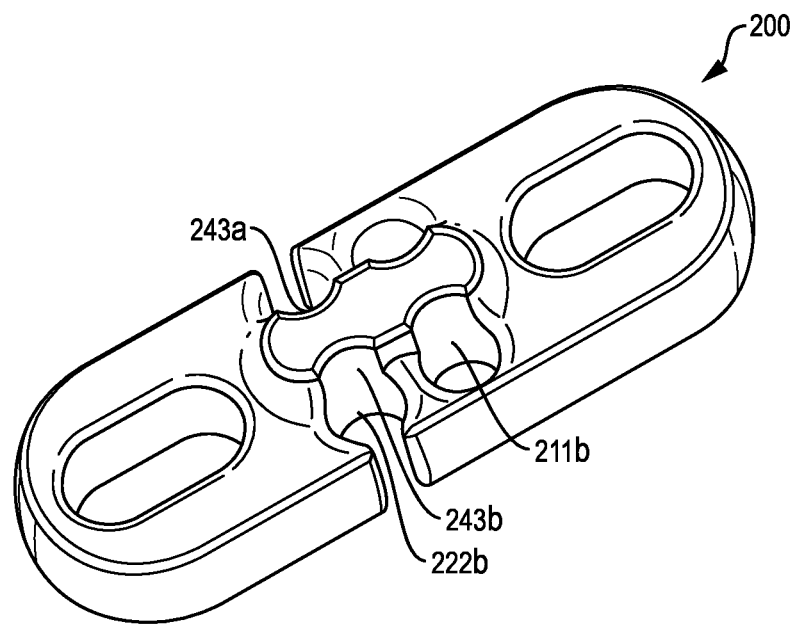
FIG. 2A illustrates a perspective view of another ribbed cortical button embodiment, in accordance with this disclosure.
Figure 2B:
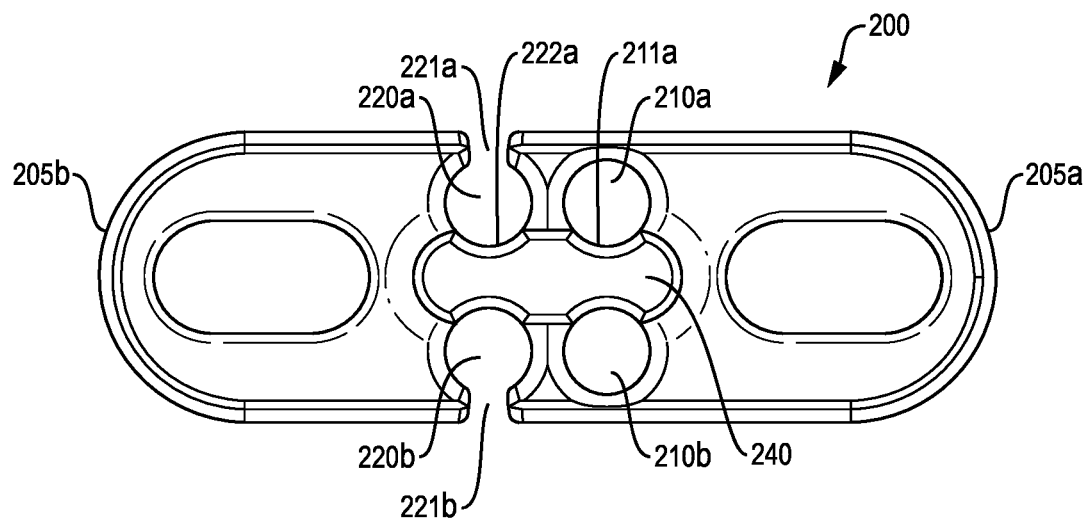
FIG. 2B illustrates a bottom view of the ribbed cortical button, in accordance with this disclosure.

FIGS. 2A and 2B illustrate another example ribbed button 200, similar to embodiment 100 except where noted. In this embodiment, apertures 210a, 210b, 220a, 220b may define circular shaped openings. Rib 240 may define lateral surfaces 243a, 243b coincident with medial edge surfaces 211a, 211b, 222a, 222b of apertures 210a, 210b, 220a, 220b. Lateral surfaces 243a, 243b may be concave surfaces. Lateral surfaces 243a, 243b may be continuous with medial edge surfaces 211a, 211b, 222a, 222b of apertures 210a, 210b, 120a, 220b and each aperture 210a, 210b, 120a, 220b may define a single curved vertical surface through a thickness of the button 200 that includes the rib 240. Stated in another way the rib 240 may conform to the shape of medial surface of apertures. Rib 240 preferably axially overlaps at least the slot lateral openings 221a, 221b. Rib 240 may extend further towards both button ends 205a, 205b than apertures 210a, 210b, 220a, 220b.

Figure 3B:
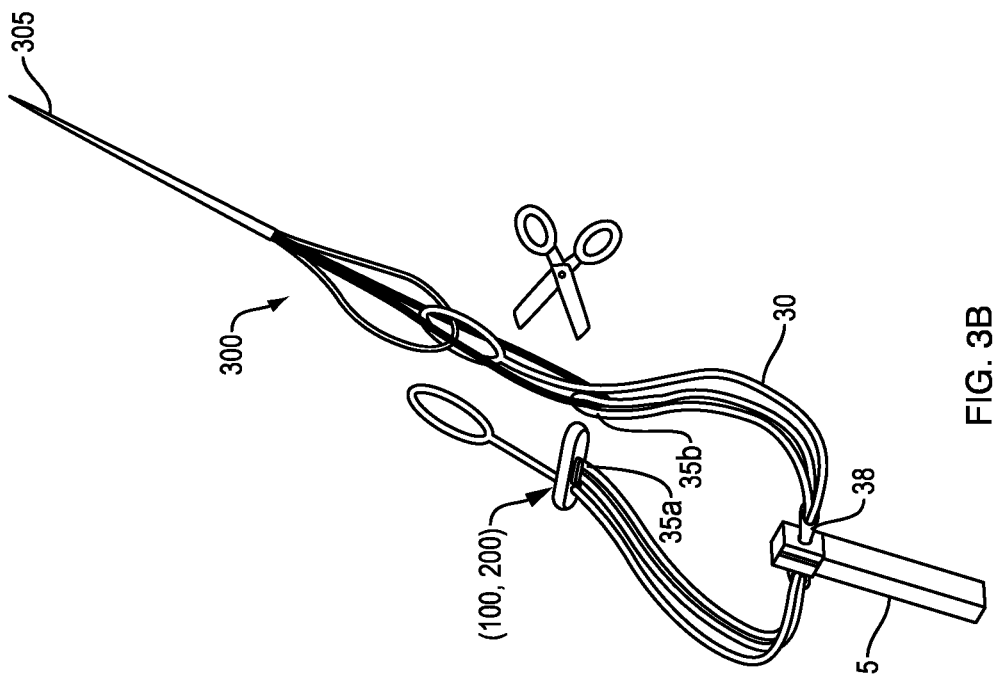
FIGS. 3A-3F illustrate an example method of coupling a graft to a ribbed cortical button, in accordance with this disclosure.
Figure 3A:
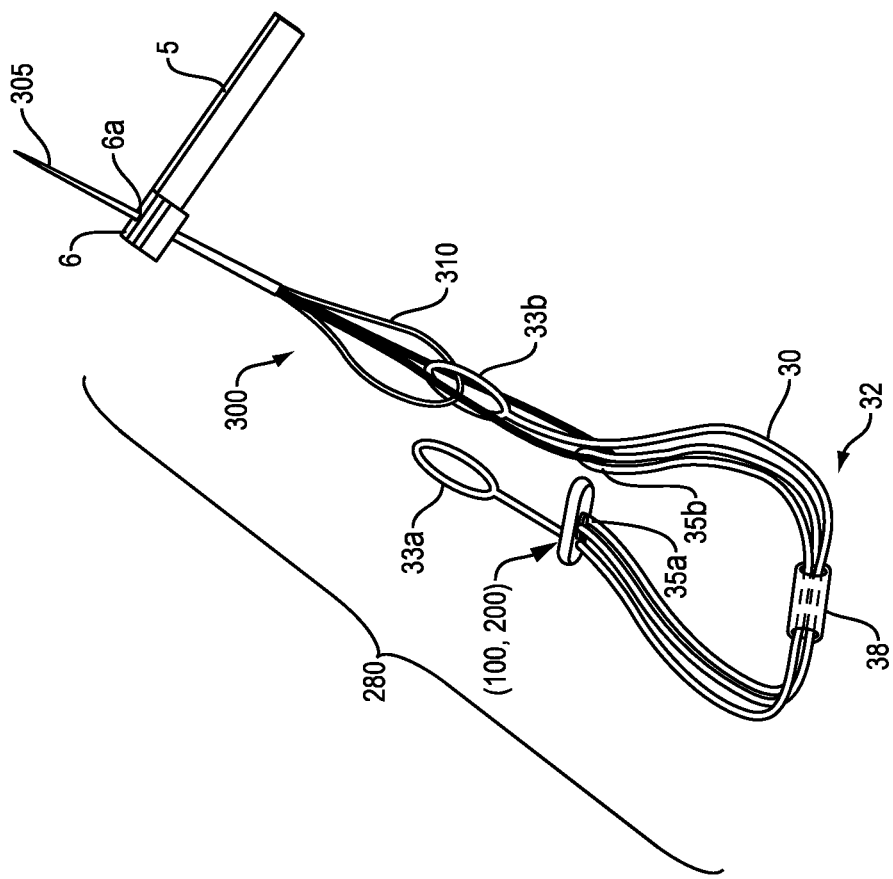
Figure 3C:
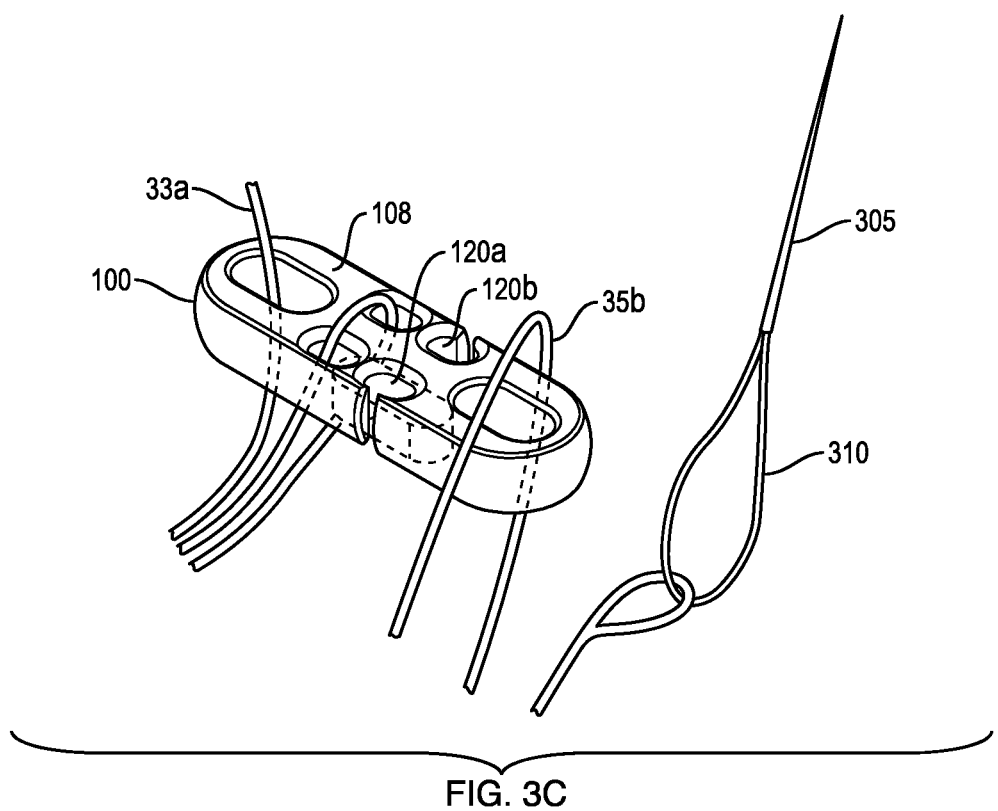
Figure 3D:
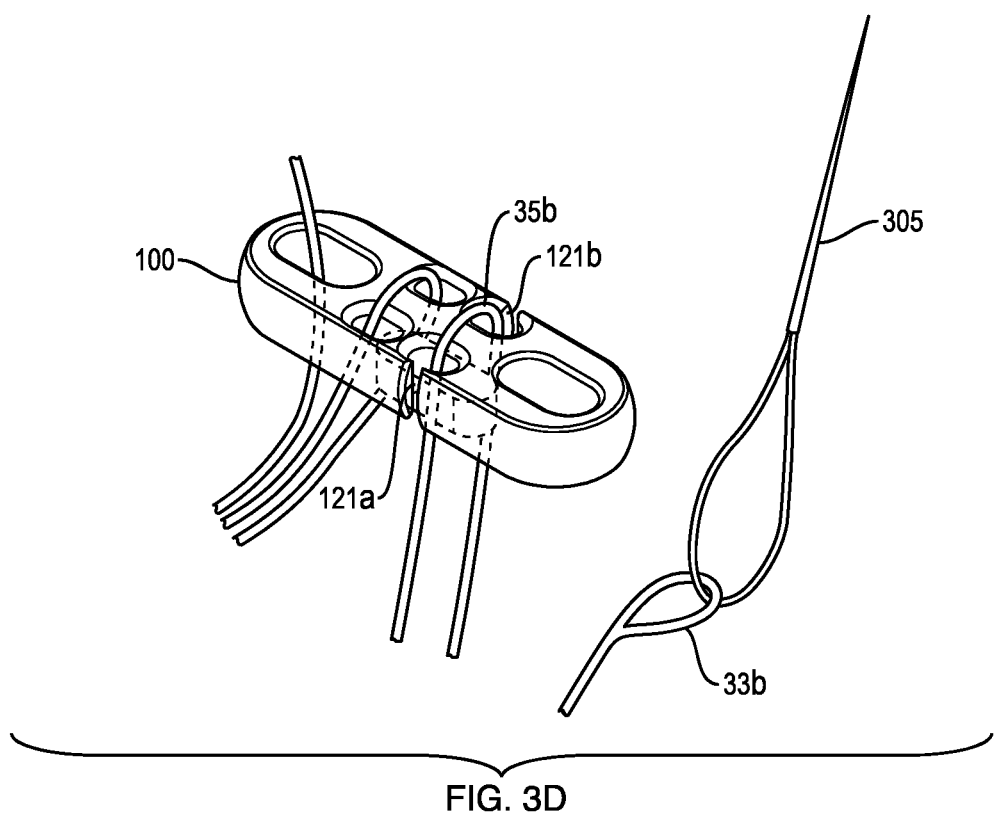
Figure 3E:
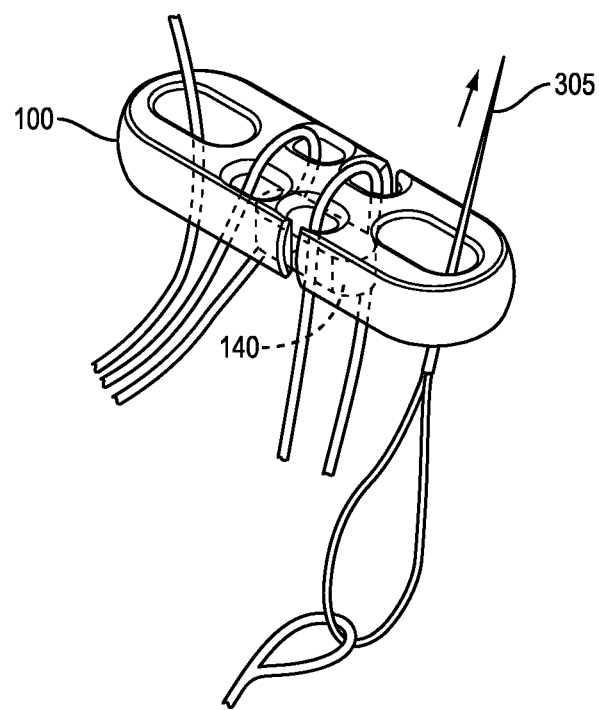
Figure 3F:
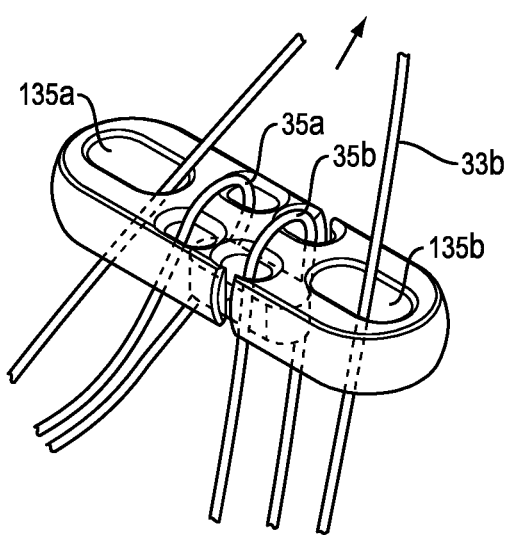
Figure 3G:
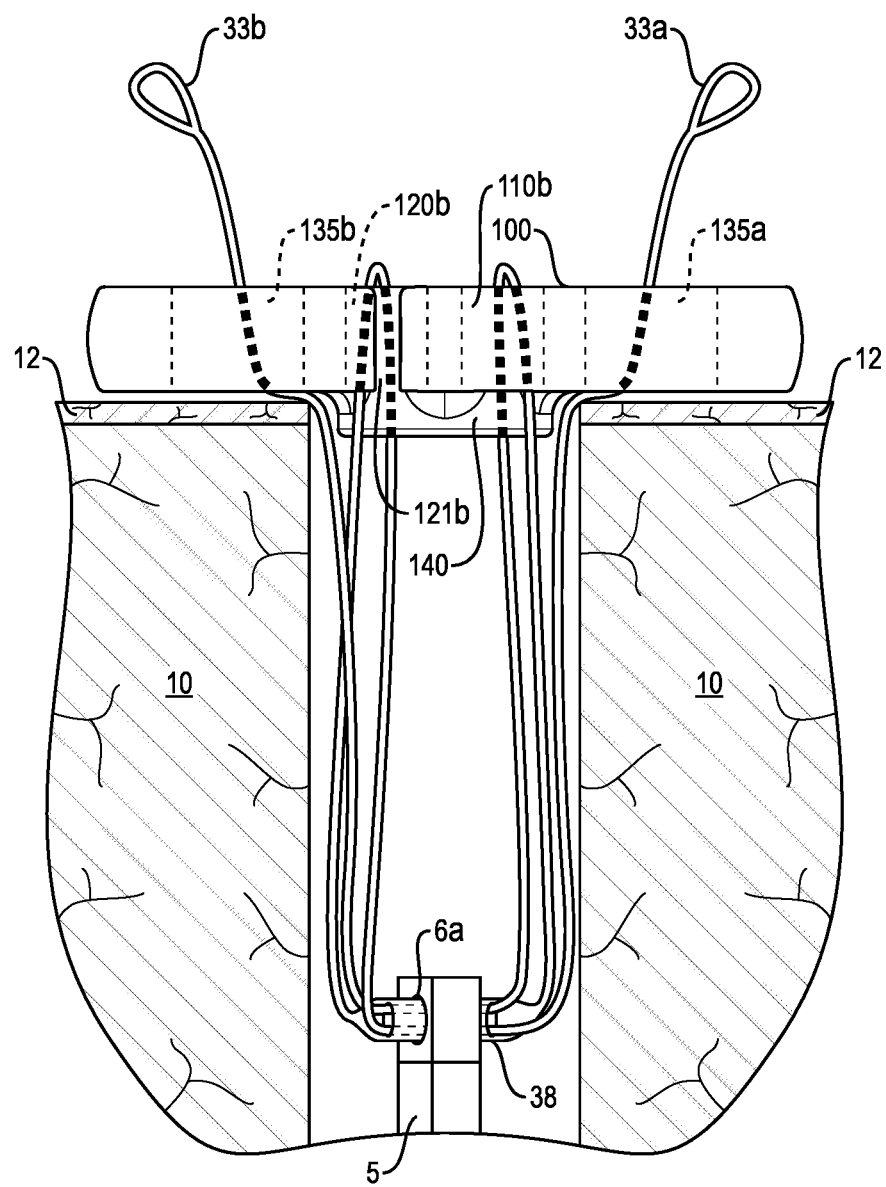
FIG. 3G illustrates a ribbed cortical button assembled with an adjustable loop construct and assembled with a bone tunnel, in accordance with this disclosure.
Figure 4A:
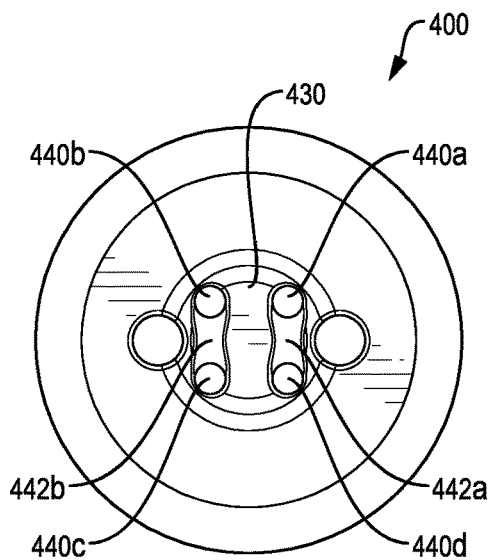
FIG. 4A illustrates a top view of a low-profile cortical button in accordance with this disclosure.
Figure 4B:
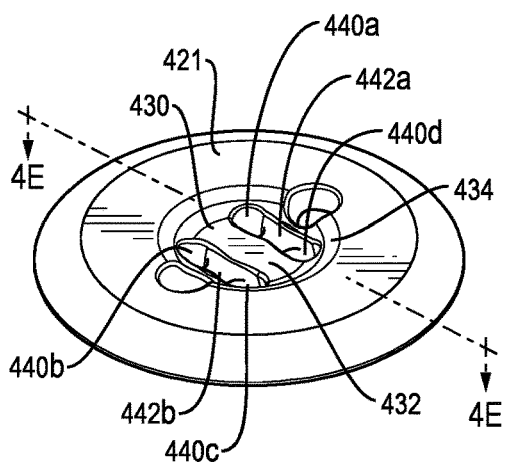
FIG. 4B illustrates a perspective view of the low-profile cortical button, in accordance with this disclosure.
Figure 4C:
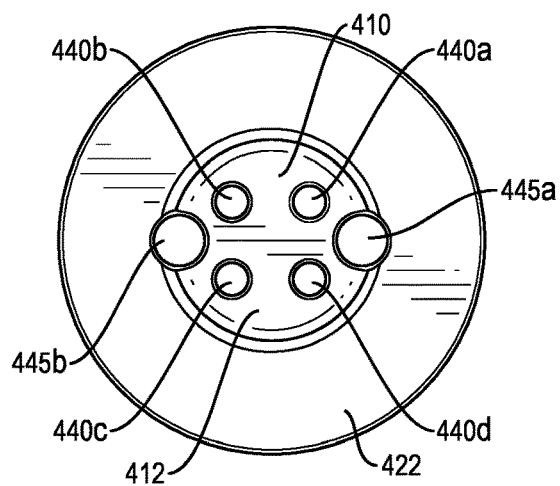
FIG. 4C illustrates a bottom view of the low-profile cortical button, in accordance with this disclosure.
Figure 4D:
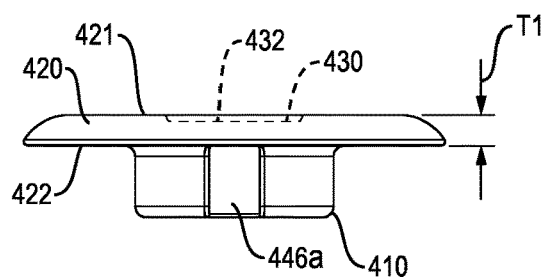
FIG. 4D illustrates a side view of the low-profile cortical button, in accordance with this disclosure.
Figure 4E:
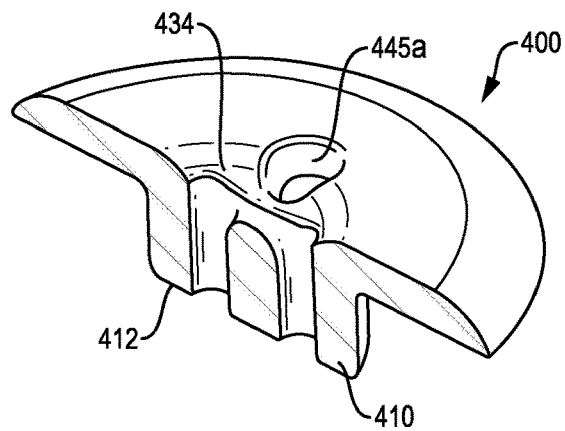
FIG. 4E illustrates a cross section view of the low-profile cortical button, in accordance with this disclosure.
Figure 5A:
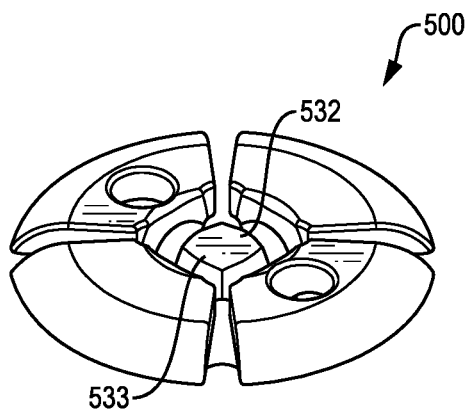
FIG. 5A illustrates a perspective view of a low-profile cortical button, in accordance with this disclosure.
Figure 5B:
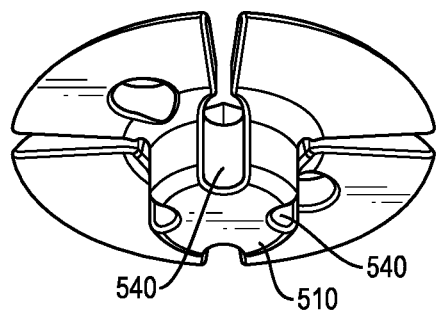
FIG. 5B illustrates another perspective view of the low-profile cortical button, in accordance with this disclosure.
Figure 5C:
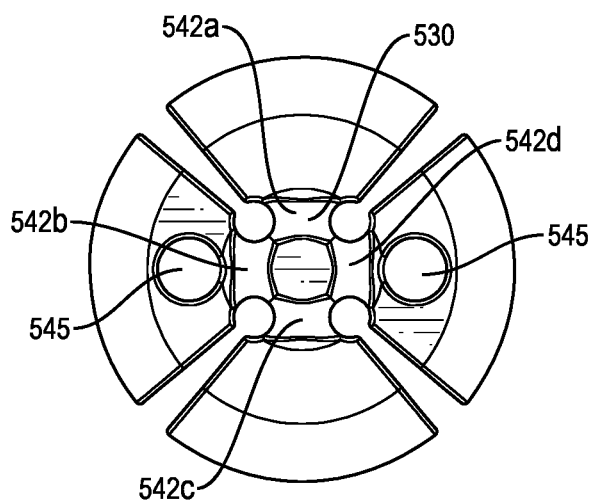
FIG. 5C illustrates a top view of the low-profile cortical button, in accordance with this disclosure.
Figure 5D:
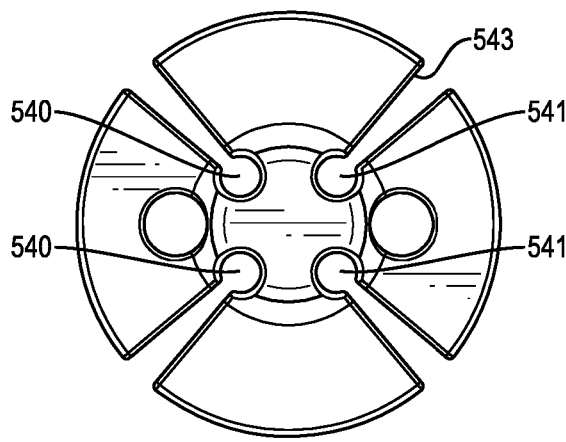
FIG. 5D illustrates a bottom view of the low-profile cortical button, in accordance with this disclosure.
Figure 5E:
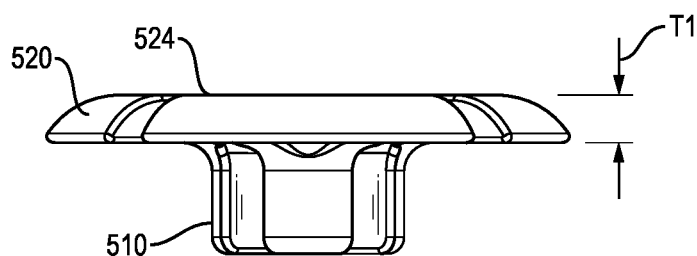
FIG. 5E illustrates a side view of the low-profile cortical button, in accordance with this disclosure.

An example method of tissue repair with a button 100 is illustrated in FIGS. 3A-3G. Button 200 may alternatively be used. To prepare for the tissue repair a tunnel 14 (FIG. 3G) through at least one bone 10 of a joint may first be formed, and a graft 5 with a bone block 6 may be obtained. A hole 6a may be drilled through the bone block 6. A suspensory fixation system 280 including a button 100 partially assembled to a flexible strand 30 may be obtained, the flexible strand 30 formed in an adjustable loop construct 32. The adjustable loop construct 32 may include a first limb or first looped end 33a and a second limb or second looped end 33b, an assembled adjustable loop 35a and a free adjustable loop 35b. Assembled adjustable loop 35a may be provided or obtained pre-assembled to the button 100 via the two apertures, similar to apertures 110a, 110b. Button 100 may include a rib 140 (not shown in FIGS. 3A and 3B for simplification of these figures). At least one locking passage 38 (as defined herein) may be formed by flexible strand 30. Button 100 may be passed through bone tunnel 14 with the assembled adjustable loop 35a preassembled. Button 100 may then be flipped to engage an external cortical surface of bone 10 (FIG. 3G).

Second looped end 33b and free adjustable loop 35b may be coupled to tissue graft 5. Second looped end 33b and free adjustable loop 35b may be obtained or provided coupled to a passing construct 300. Passing construct 300 may be passed through bone block hole 6a to draw looped end 33b and free adjustable loop 35b through the bone block 6. Passing construct 300 may be passed through bone block hole 6a to draw locking passage 38 through bone block hole 6a and place locking passage 38 within the bone block hole 6a. Bone block hole 6a may be sized to receive the locking passage 38, and the locking passage 38 may include at least three lengths of flexible strand 30. After coupling the adjustable loop construct 32 to the graft 5, free adjustable loop 35b may be separated from passing construct 300 (FIG. 3B) and looped over the top side 108 of button (button 100 shown) and into slotted apertures 120a, 120b, as shown in FIG. 3C-3D. While inserting free adjustable loop 35b into slotted apertures 120a, 120b, looped end 33b may remain coupled to passing construct 300. Looped end 33b may then be inserted through aperture 135b (FIG. 3E-3F) using the passing construct 300, before separating passing construct 300 from looped end 33b. Suspension construct is now coupled to graft 5 and is in a closed assembly configuration, with the looped end 33b and adjustable loop end 35b assembled to button 100 and the passing construct 300 separated therefrom. Suspension construct in the closed assembly configuration may then be passed through the bone tunnel 14.

Looped end 33b may be inserted through aperture 135b, using threading member 305 of passing loop construct 300 (FIG. 3G). Tension on limb ends 33a, 33b may reduce the adjustable loop construct 32 to draw graft 5 towards button 100. FIG. 3G illustrates button 100 engaged over a bone tunnel 14 formed through bone 10 and engaging a cortical layer of bone 12. Rib 140 extends into bone tunnel 14. For a tunnel diameter of 4.5 mm, the rib 140 may preferably have a length $L_R$ that is less than 4.5 mm. Rib 140, 240 may be approximately 3.5 mm in length $L_R$ leaving room for limb ends 33a, 33b to route around rib 140, 240 and extend through apertures 135a, 135b. Rib 140 may be between 1-2 mm wide and may more preferably be approximately 1.3 mm wide. Rib 140, 240 may extend into the bone tunnel 14 between 1-2 mm.

In alternative methods, the adjustable loop construct 32 may be coupled to another tissue anchor instead of or in addition to a tissue graft 5. For example, the method may include coupling the other tissue anchor to the adjustable loop construct 32 and then coupling the tissue anchor to a second bone. The second bone may be a different bone to bone 10, or a different segment of bone 10. The adjustable loop construct 32 may draw the other tissue anchor towards the button 100 to fix the second bone in place. The other tissue anchor may be a second cortical button or soft anchor.

FIGS. 4A-4E and 5A-5E illustrate example cortical buttons 400 and 500 that may have a circular profile. These cortical buttons 400, 500 define an outer boundary that is approximately circular, the outer boundary configured to engage an external bone surface and prevent entrance of the button 400 and 500 into the bone tunnel. Contrary to buttons 100 and 200 however, buttons 400 and 500 are non-passing buttons defined in that they are not configured to have a profile that has a small cross section profile than when deployed to provide the ability to pass it through a bone tunnel of limited diameter. While a larger bone tunnel could be formed to pass these buttons (400, 500) therethrough, the tunnel diameter for a circular profile button would also remove the bone external surface that the button would engage once flipped. As such, buttons 400 and 500 are configured to remain external to the bone tunnels throughout the procedure. Buttons 400 and 500 may be similar to some embodiments disclosed in commonly owned PCT patent application number PCT/US20/038401 filed Jun. 18, 2020, herein incorporated by reference in its entirety.

Buttons 400 and 500 may be preferable for bone locations close to the patient's skin. A portion of the button 400, 500 sits proud of the bone surface which may be easily palpable, these portions configured to have a low and tapered profile to reduce palpability. For example, in ACL repair, buttons 400 and 500 may engage the tibial side of the repair. Buttons 400, 500 define a dome shaped top surface with a tapering outer periphery to maintain a reduce profile. Buttons 400, 500 define a maximum dome thickness T1 that sits proud above the bone external surface that is minimized for reduced palpability. Circular buttons have improved stress distribution around the bone/button interface, which allows them to be thinner (T1) relative to oblong buttons 100 and 200, for example.

Button 400 includes a post 410 (FIG. 4D) concentric with its dome portion 420 and extending from a lower surface 422 of dome portion 420. Lower surface 422 may define a flat planar surface for engaging an external surface of the bone. Dome portion 420 may include an annular planar surface 421 that lies parallel to lower surface 422. Dome portion 420 may also include a recess 430 for receiving flexible strands 30 therein such that the flexible strands 30 lie at least partially within the recess 430, reducing their palpability. Recess 430 is disposed towards the center of dome portion 420 and includes a plurality of apertures 440a, 440b, 440c, 440d therethrough that provide passage for at least one flexible strand 30 therethrough. Button 400 includes four apertures 440a, 440b, 440c, 440d, each defining 360 degree bounded holes. Each aperture 440a, 440b, 440c, 440d may have the same diameter. The boundaries of all apertures 440a, 440b, 440c, 440d may be disposed entirely within recess 430. Apertures 440a, 440b, 440c, 440d may extend through post 410, having an aperture exit at a bottom surface 412 of post 410. All four apertures 440a, 440b, 440c, 440d may be entirely enclosed within post 410. apertures 440a, 440b, 440c, 440d may be equally spaced from each other. Apertures 440a, 440b, 440c, 440d may be arranged in an approximate square or rectangular arrangement, where each aperture defines an apex of the arrangement. Apertures 440a, 440b, 440c, 440d may define a first pair 440a, 440d and a second pair 440b, 440c, each pair defining ends of a strand channel 442a, 442b therebetween. Strand channel 442a, 442b extends below a bottom surface 432 of recess 430. Strand channels 442a, 442b at least partially nests a portion of the flexible strand 30 therein. Strand channels 442a, 442b define pulley surfaces that the flexible strand 30 may slide along. This may reduce a flexible strand of an adjustable loop construct. Strand channels 442a, 442b may each define convex curved surface along their length, corresponding to the curves of the strand loops (seen best in FIGS. 4B and 6B).

Recess 430 defines a periphery 434 that may be circular and concentric with dome periphery. Periphery 434 may be intersected by a third pair of apertures 445a, 445b. The third pair of apertures 445a, 445b extend through and along an outer circumferential surface of the post 410. Apertures 445a, 445b each therefore have a first axial length portion that is fully enclosed, defining a 360 degree bounded hole that is formed entirely by the dome portion 420. Apertures 445a, 445b also include a second axial length portion extending from and continuous with the first axial length portion, that is not fully enclosed, and defines an axial channel (446a shown) bounded by the post 410, best seen in FIG. 4D. A first of the third pair of apertures 445a is disposed between the first pair 440a, 440d and radially spaced therefrom. A second of the third pair of apertures 445b is disposed between the second pair 440b, 440c and radially spaced therefrom. The third pair of apertures 445a, 445b may be equal to each other in diameter and both may be larger in diameter than apertures 440a, 440b, 440c, 440d. Button 400 is configured to be provided pre-assembled to a flexible strand construct.

FIGS. 5A-5F illustrate another embodiment of a button 500 that may have a circular or slightly oval shaped dome 520 and post 510 extending therefrom. Button 500 may be a non-passing button and may include radial slotted openings 540/543 for receiving a flexible strand therethrough and therefore coupling to a flexible strand construct during the procedure. Similar to button 400, button 500 includes a recessed central portion 530 for recessing the flexible strand therein, to reduce palpability. Button 500 is similar to button 400, except when noted. For example, button 500 includes four channels or pulley surfaces 542a, 542b, 542c, 542d. Channels or pulley surfaces 542a, 542b, 542c, 542d may all be orthogonal to each other, forming a square or rectangle around a central recess post 532. Having four channels 542a, 542b, 542c, 542d give the user more flexibility while assembling the flexible strand construct. Recessed post 532 may define a top surface 533 that is planar and recessed below a top surface 524 of dome portion 520.

Button 500 includes a plurality of openings that are slotted openings 540. Slotted openings 540 extend radially from an end of a channel or pulley surface (542a, 542b, 542c, 542d) radially up to and including an outer periphery of dome portion 520. Openings 540 define a dock portion 541 within which the flexible strand (30) nests, with a tapered opening portion 543 extending radially therefrom. Tapered opening portion 543 may be linearly ed to a larger opening at the dome periphery. Dock portion 541 extends vertically through a thickness of dome portion 520 and at least partially through a thickness of post 510. Dock portion 541 may extend through and interrupts a circumferential outer surface of post 510, as seen best in FIGS. 5B and 5E. Post 510 may be configured to fit within a bone tunnel and may be a close or sliding fit with the bone tunnel. Outermost apertures 545 define a pair of apertures that may define 360-degree bounded apertures and may be larger in diameter than dock portion 541. Button 500 may be provided in a variety of sizes. In some larger button sizes, the post 510 may have a larger diameter or width and outmost apertures 545 may intersect with post 510. In an example smaller button size, the post 510 may be entirely medially spaced from the outermost holes 545 and therefore the post 510 and holes 545 do not intersect.

Figure 6B:
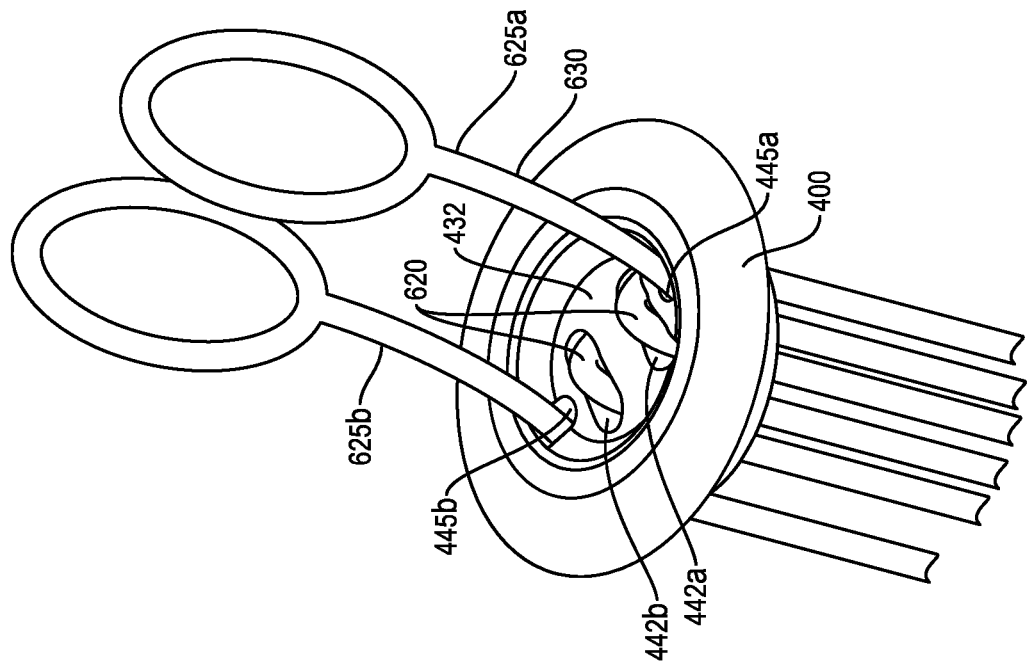
FIG. 6B illustrates a closer view of an adjustable loop construct coupled to a low-profile cortical button, in accordance with this disclosure.
Figure 6A:
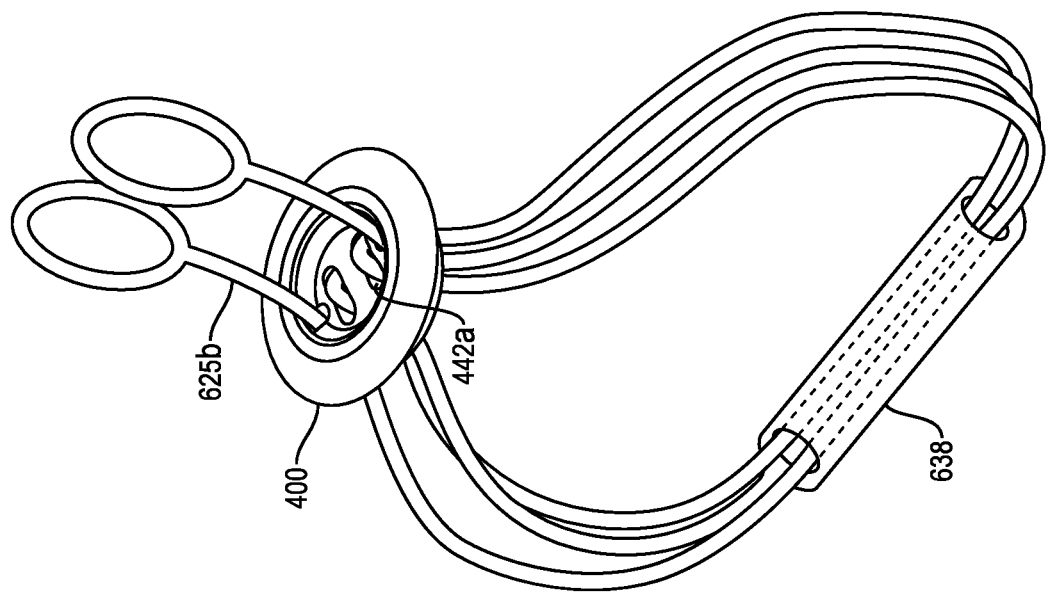
FIG. 6A illustrates a view of an adjustable loop construct coupled to a low-profile cortical button, in accordance with this disclosure.

FIGS. 6A and 6B illustrate a system including a button 400 and flexible strand 630. Flexible strand 630 may be provided assembled to button 400 and may include at least one locking passage 638 therealong. FIG. 6B shows two loop ends 620 extending through the two pair of apertures 440a, 440b, 440c, 440d and each aperture including a single length of strand 630 therethrough. Tension will nest the loops 620 within the corresponding channels 442a, 442b, that may be contoured, defining convex curved surfaces for engaging loops 620. Limbs 625a, 625b may extend through the third pair on apertures 445a, 445b. Tension on the limbs 625a, 625b may slide the loops 620 through corresponding channels and reduce the overall loop lengths. Stated in another way, tension on the limbs 625a, 625b may draw the locking passage 638 towards the button 400.

In a similar manner shown in FIGS. 6A-6B, button 500 may be provided operatively coupled to an adjustable loop formed with a flexible strand 630, in a similar manner to that shown in FIGS. 6A-6B. For all inside techniques the surgeon may detach or disassemble at least one of the loops 620 from the button 500 via slots 540. Button 500 may be completely removed from flexible strand 630, and at least one loop 620 and limb 625a may be passed through the joint and then re-assembled with the button 500 (via pulleys) to create the fully assembled loops once again.

Adjustable Loop Embodiments

Figure 7:
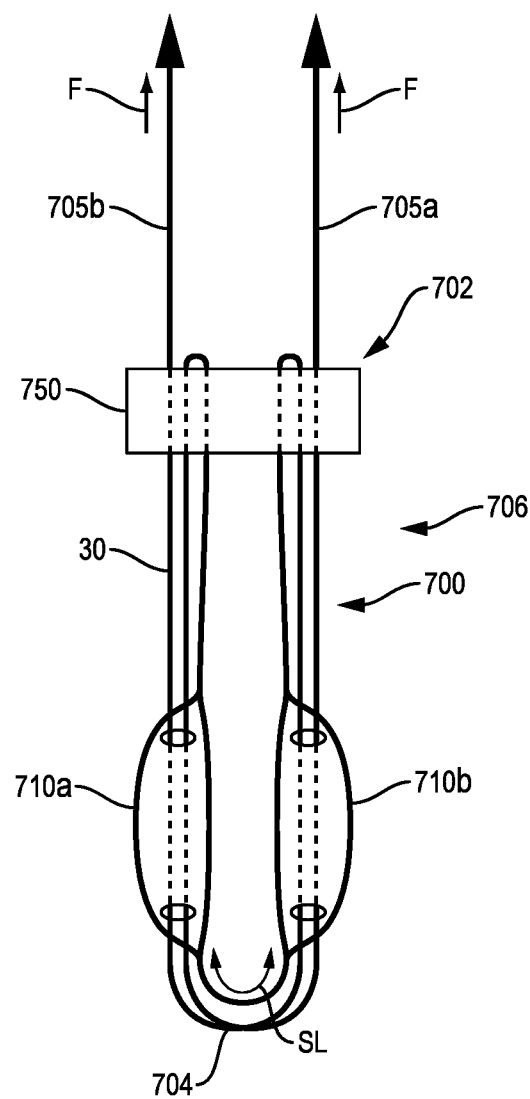
FIG. 7 illustrates an adjustable loop construct with two locking passages in accordance with this disclosure.

FIG. 7 illustrates an adjustable loop construct 700 that may include two locking passages 710a, 710b, and may be assembled or partially assembled to an anchor, such as a cortical button 750. Adjustable loop construct 700 may be formed from a flexible strand 30. Adjustable loop construct 700 may be preassembled to at least one side of button 750, together defining an adjustable suspensory fixation system 706. Adjustable loop construct 700 may be formed from a single length of a flexible strand 30. Button 750 may be any button disclosed herein, or other cortical buttons known in the art such as for example, buttons disclosed in commonly owned PCT patent application number PCT/US20/038401 filed Jun. 18, 2020, or commonly owned U.S. Pat. No. 10,383,617 both references incorporated by reference in their entirety.

Adjustable loop construct 700 may define a portion of an adjustable suspensory fixation system 706 for ligament reconstruction or repair. During tissue repair, saddle end 704 may couple to a body, the body being at least one of, but not limited to a tissue component or a surgical component; the tissue component being for example a ligament or graft; the surgical component may be a tissue anchor, or another flexible strand. For example, the adjustable suspensory fixation system 706 may couple a first bone to a second bone and may have another tissue anchor operatively coupled to saddle end 704 (not shown here). Body may be coupled to loop saddle end 704 between the two locking passages 710a, 710b.

Adjustable loop construct 700 may be formed by flexible strand 30 that is braided suture, braided to be hollow defining an elongate passage therealong. Adjustable loop construct 700 first end 702 may be assembled to button 750 and an opposite saddle end 704 may be coupled to a body as defined herein. Adjustable loop construct 700 includes two locking passages 710a, 710b spaced away from the saddle end 704. Relative to the construct 32 shown in at least FIG. 3A, that includes a single locking passage 38, two locking passages 710a, 710b may provide similar knotless locking strengths (withstand similar physiological cyclic loading), but two locking passages or split locking passages may offer several advantages. For example, this configuration of locking passages 710a, 710b may allow the construct 700 to be reduced in loop perimeter with lower forces or tensions on ends 705a, 705b relative to a construct with a single locking passage. This is a result of the locking passages 710a, 710b being approximately linear (not curved or bent) and approximately parallel to the reduction force direction (F) on ends 705a, 705b. In comparison, locking passage 38 is curved as it loops around the construct end. During reduction, strands 30 slide through the corresponding locking passage. Maintaining a linear locking passage allows the strands 30 to slide linearly and reduce strand cinching from a kink or curve along the locking passage. Furthermore, coupling a saddle end 704 free of a locking passage to a body may be easier. The inventors have found that the inherent increased outer diameter of a locking passage may add significant force and/or tissue tearing while threading through the body (as defined herein). Larger tunnel opening sizes may be required through tissue anchors for example, to fit the locking passage. In the case of soft tissue grafts, larger needles and/or higher forces may be needed to thread the locking passage through the soft tissue.

The inventors have also found that the spacing length (SL) or linear distance along the strand 30 between the two locking passages 710a, 710b preferably has an upper length limit. Consider that when reducing the adjustable loop construct 706, the shortest the loop construct may reduce to, or a minimum reduced loop length is limited by the fixed length portions of the adjustable loop construct. These include at least the lengths of the two passages 710a, 710b and spacing length SL between the two passage 710a, 710b. Depending on the length of tissue or graft, or anatomy of the repair, significant reduction may be preferable. Depending on the length of tissue or graft, or anatomy of the repair, a short final reduction length may be preferable. Therefore, the shorter the two locking cradles 710a, 710b and spacing length SL are, the smaller the adjustable loop construct can become, with reduction. A shorter length of the locking passages 710a, 170b and spacing length SL may provide an adjustable loop construct that accommodates a wider range of graft or tissue configurations. Locking passages 710a, 710b however require a minimum length to securely cinch and knotlessly lock the adjustable loop 706. The locking passages 710a, 710b therefore define a length of the adjustable loop construct 700 that is not adjustable and provides sufficient locking forces on the adjustable suture loop 700, capable of withstanding the physiological loading. This length may depend on the flexible strand material and properties. In some example embodiments, each locking passage 710a, 710b may be between 0.5-1.5 inches long, and may more preferably be approximately 0.75 inches long.

The spacing SL is preferably also short to avoid adding unnecessary length to a minimum reduced loop length of the adjustable suture loop 700. Spacing length SL is preferably sufficient to split the two locking passages 710a, 710b to reduce adjustable loop reduction forces F. The spacing length SL between the two locking passages as measured along the strand 30 linearly (see FIG. 8A) between the two locking passages 710a, 710b may be between 0.10-0.5 inches, and may, in some procedures be approximately 0.25 inches.

FIG. 8A-8C demonstrate the steps to forming the construct 700. Beginning with FIG. 8A, a length of a flexible strand 30 is shown. Locations of locking passages 710a, 710b are shown as enlarged or dilated portions for clarity of discussion. However, as provided, these locations may be similar in diameter and shape to the remaining length of the strand 30 and the act of spicing the strand 30 and extending the strand 30 through itself may dilate that portion of the strand 30. A snare loop (not shown) may extend along passages 710a, 710b. A dilating means (not shown) may be first extended through passage locations.

Turning now to FIG. 8B, end 705b may be extend into and along the strand 30 at a locking passage location 710b and exit the passage 710b for a length (approximately SL) before extending into and along strand 30 at locking passage location 710a. This forms a first eyesplice loop 708b and limb 705b. The length SL between the two locking passages 710a, 710b may be selected, depending on the procedure or application. For example, if the saddle end 704 is configured to couple to a graft, the saddle length SL may be long enough the wrap around the graft width, with the locking passages 710a, 710b disposed along a side of the graft. As a second example, if the saddle end 704 is configured to couple to a tissue anchor, the length SL may be long enough to couple to the anchor, placing the locking passages 710a, 710b outside of the tissue anchor, and will depend on the anchor configuration. While forming this first eyesplice loop 708b, the loop may be threaded through apertures of a button, such as for example apertures 110a, 110b in FIG. 1A. First eyesplice loop 708b may therefore directly coupled to a button anchor 750. This may assemble the construct 700 with a button. As shown eyesplice loop 708b is short, for simplicity of the figure, however length of loop 708b may be of any length.

FIG. 8C shows formation of a second eyesplice loop 708a. Limb end 705a may extend into and along the strand 30 at locking passage 710a first, forming the second eyesplice loop 708b. Limb end 705a may than extend for a length along saddle end 704 before extending into and along strand 30 at locking passage 710b. Second eyesplice loop 708a may also thread through apertures of a button, such as for example button 400. This assembles both loops 708a, 708b to a button. In other embodiments, at least one of the loops 708a, 708b may define a free looped end, and be looped over and through slotted openings of the button during the procedure. Buttons 100, 200 or 500 show slotted openings that allow for selective assembly with at least one of the eyesplice loops 708a, 708b from the button. On other examples, at least one loop and limb (708a, 708b, 705a, 705b) may be operatively coupled to a threading member such as a shaft, rod or needle (example passing construct 300 shown in at least FIG. 3A). Threading member may be configured to insert a loop and/or limb of the construct 700 through a body such as a tissue, a graft or a tissue anchor for example.

In this construct 700, each locking passage 710a, 710b includes two lengths of strand 30 extending therethrough. The two lengths of strand 30 cross over each other to exit from opposite ends of each locking passage 710a, 701b. In other embodiments, each limb may only extend through one locking passage 710a, 710b. For example, limb 705b may extend through passage 710b only to form eyesplice loop 708a. The distance between to the two discrete locking passages 710a, 710b may be sufficient to suspend a graft thereover, or extend through a thickness of tissue, or through an anchor. Saddle end 704 may include three strand lengths of strand 30, two of which are slideable and one single strand which is static or fixed (non slideable) and extends directly from, and is continuously braided with both locking passages 710a, 710b.

Figure 9A:
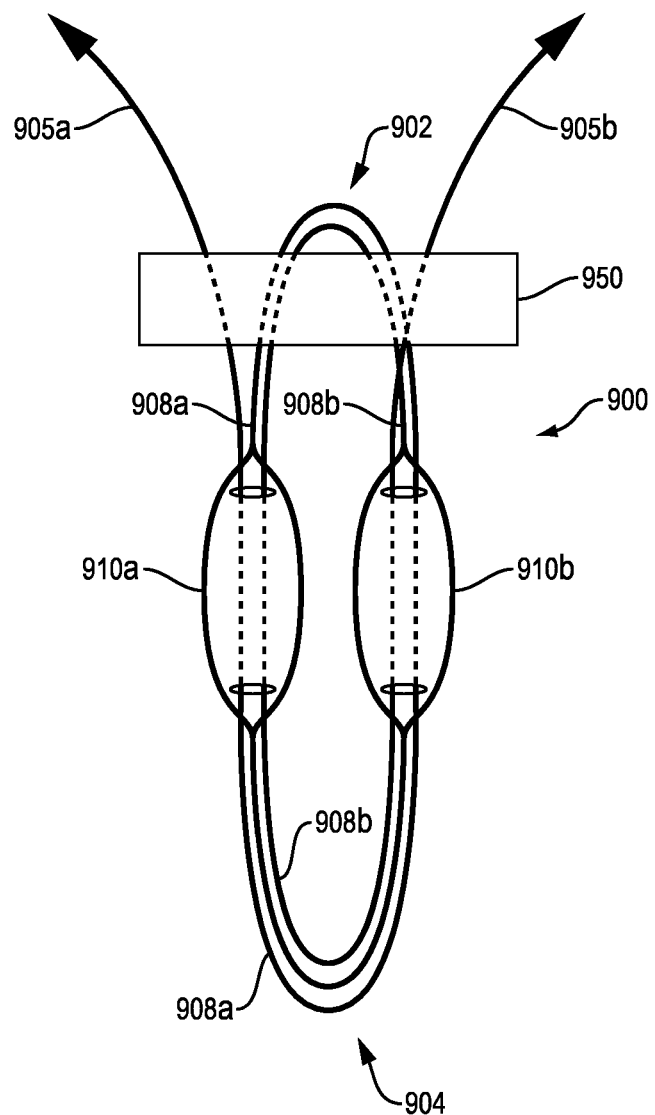
FIG. 9A illustrates another adjustable loop construct with two locking passages in accordance with this disclosure.

FIG. 9A illustrates another adjustable loop construct 900 that may form a plurality of adjustable loops and may include two locking passages 910a, 910b. Adjustable loop construct 900 may define an adjustable suspensory fixation device for ligament reconstruction or repair. In other examples, construct 800 may define an adjustable coupling means between a first and second bone and may have a tissue anchor operatively coupled to a portion of the construct 900 (not shown here).

Adjustable loop construct 900 may be formed by a braided suture that may be hollow to define an elongate passage therealong. The two locking passages 910a, 910b are formed by splicing the suture through itself, which under tension forms a knotless locking mechanism and prevents the loop from expanding. The adjustable loop construct defines first end 902 that may be assembled to a button 950 and an opposite saddle end 904. Adjustable loop construct 900 may have locking forces with reduced loop reduction forces similar to construct 700.

The steps of forming construct 900 may begin with strand 30, similar to that shown in FIG. 8A with similar locations and philosophies for locking passages. However, compared to FIG. 8B, the loops are formed differently. Shown in FIG. 9B, forming the adjustable construct 900 may include extending end 905b through an aperture of a button 950

(shown in FIG. 9A) and then through the strand 30 at location identified as 910a first, preferably on a side adjacent end 905a and then exit the passage 910a adjacent saddle 904. End 905a then extends along saddle 904 for a length before extending along strand 30 at locking passage location 910b. This forms a first loop 908b and limb 905b. While forming this loop 908b, the loop may be threaded through apertures of a button, such as for example apertures 110a, 110b in FIG. 1A. Another button example is disclosed in commonly owned U.S. Pat. No. 10,383,617 both references incorporated by reference in its entirety. Each aperture preferably provides passage for a single strand of suture therethrough. This assembles the construct 900 with a button. A second loop 908a may be formed in a similar manner to the first loop 908b and is shown in FIG. 9C. Limb end 905a extends through the strand 30 at locking passage 910b first then across the saddle 904 before extending along strand 30 at locking passage 710a.

Figure 10:
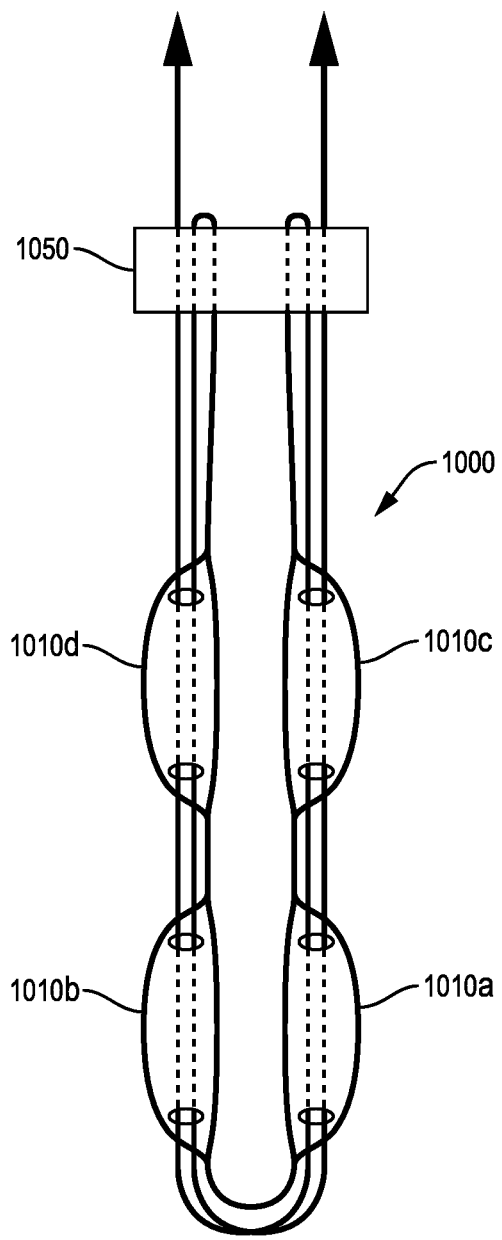
FIG. 10 illustrates another adjustable loop construct with four locking passages in accordance with this disclosure.

FIG. 10 illustrates another example construct 1000, that may be assembled with a button 1050 and may include four locking passages 1010a, 1010b, 1010c, 1010d.

Figure 14:
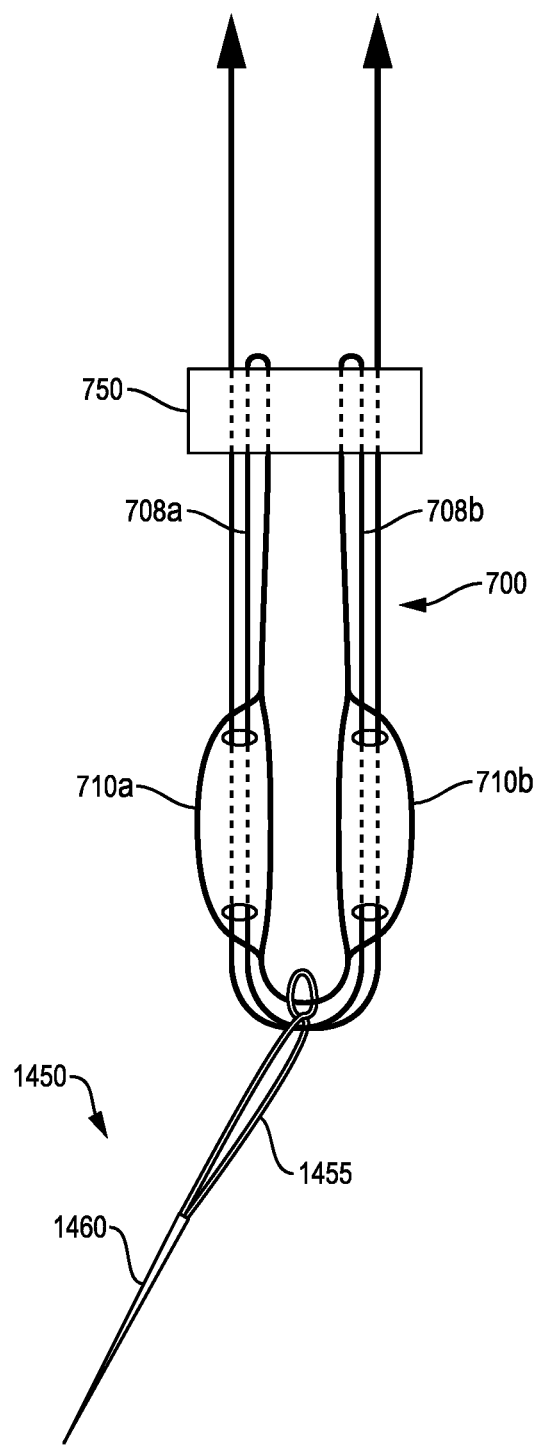
FIG. 14 illustrates an adjustable loop construct with a passing loop construct coupled thereto, in accordance with this disclosure.

In some embodiments, adjustable loop construct 700 may be provided assembled to a button 750 in a fully assembled configuration (also termed a closed loop configuration). Unlike the construct illustrated in 3A-3D, both loops 708a, 708b may be preassembled to button 750. Button may include four 360 degree (°) bounded holes and therefore disassembly of a loop 708a, 708b may not be available, without deconstruction of the adjustable loop. In some embodiments, when provided in a closed loop configuration, adjustable loop construct 700 may include a passing construct 1450 coupled to the saddle end 704, as illustrated in FIG. 14. The passing construct 1450 is configured to draw the adjustable loop construct 700 through a tissue or graft.

Passing construct 1450 may include a loop 1455 formed of a flexible strand such as a wire or suture. Loop 1455 may be coupled to a threading member 1460 and loop 1455 may having a fixed length (non-adjustable). Threading member 1460 may be a rigid needle that pierces the tissue or graft. Threading member 1460 may be configured to pass through apertures of another tissue anchor (not shown) or prepared tunnels through bone. Threading member 1460 may be configured to pierce a tissue or graft and draw the loop 1455 followed by the saddle end 704 of adjustable loop construct 700 therethrough.

Loop 1455 may originate as a length of suture or wire, with two terminal ends that are swaged or crimped to threading member 1460, to form the loop 1455. Loop 1455 may be formed of a flexible strand that is different or separately formed from flexible strand 30. Passing construct 1450 may be coupled to the three strand lengths of the saddle end 704 with a complex loop. The complex loop may be configured to sequentially draw the three strand lengths through the tissue. Sequentially drawing the strand lengths of the saddle end 704 may reduce tissue damage or deformation, and reduce forces required to draw the saddle end 704 through the tissue or graft. This passing construct 1450 may couple the saddle end 704 to the tissue or graft. The complex loop may be configured to limit sliding of the passing construct 1450 along the adjustable loop construct 700. The complex loop may help to control the three length strands and maintains them in close approximation as they slide relative to each other, as explained further herein.

Figure 15:
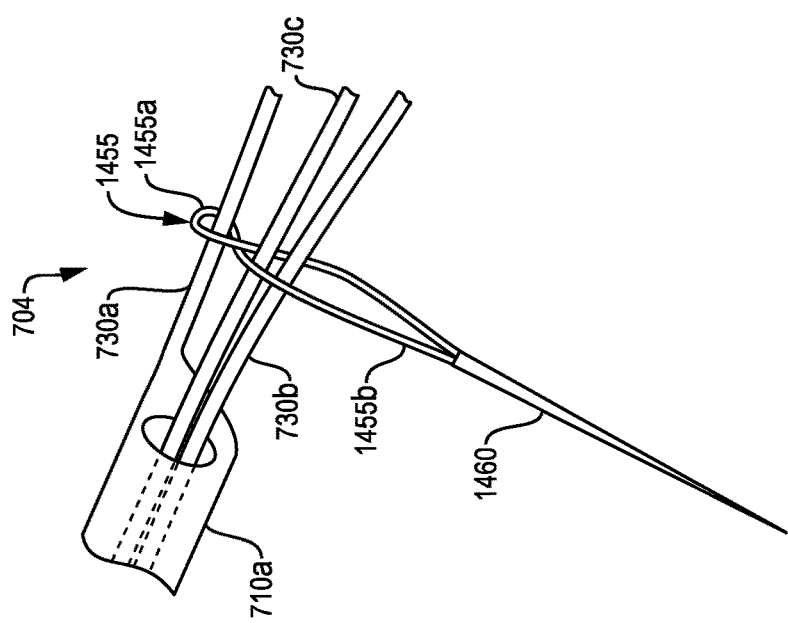
FIG. 15 illustrates a saddle portion of an adjustable loop construct with a passing loop construct coupled thereto with a figure-of-eight, in accordance with this disclosure.

Loop 1455 may form a complex loop around the saddle end, such as a figure-of-eight loop as illustrated in part in FIG. 15. FIG. 15 illustrates a first locking passage 710a, with the three strand lengths extending therefrom. Strand length 730a defines a static strand, in that it is directly coupled to and extends from both locking passages 710a, 710b. While reducing the adjustable loop construct 700, strand length 730a does not slide. Strand length 730a may be continuously braided with locking passages 710a, 710b and therefore does not extend through and slide through locking passages 710a, 710b. Strand lengths 730b, 730c are dynamic strands, each strand 730b, 730c continuous with a limb 705a, 705b. Drawing on limbs 705a, 705b slides dynamic strand lengths 730b, 730c through the passages 710a, 710b to reduce the adjustable loop perimeter.

Loop 1455 may form a first loop 1455a of the figure-of-eight loop around the static strand 730a, and second loop 1455b of the figure-of-eight loop may wrap around both dynamic strands 730b, 730c. The figure-of-eight configuration may limit sliding of the passing construct 1450 along and around the adjustable loop construct 700. Sliding off-center may need correction by the user during stitching. The first loop 1455a of the figure-of-eight is limited to sliding only along the static strand 730a, and the extent of sliding is bounded by the locking passage 710a, 710b. Limiting sliding may avoid asymmetry as the adjustable loop construct 700 is threaded through a tissue or graft. The figure-of-eight loop configuration is configured to maintain the passing construct 1450 between the two locking passages 710a, 710b. Without the figure-of-eight loop formation, loop 1455 may slide over one of the locking passages 710a, 710b and draw that locking passage first into and through a graft or tissue. As explained earlier, this may increase the forces required to couple the adjustable loop construct 700 to the graft of tissue. In addition, if the loop 1455 was not a figure-of-eight loop and wrapped around just the static strand length 730a, the dynamic strand lengths 730b, 730c may trail too far behind when passing through tissue/graft, creating confusion during stitching and uneven adjustment of the construct 700. The figure-of-eight loop may first pass the dynamic strand lengths 730b, 730c through a graft, followed by the static strand length 730a, followed by the two locking passages 710a, 710b. The second loop 1455b is configured to contain the two dynamic strand lengths in close apposition while passing the saddle end 704 through the tissue/graft, which may reduce confusion during stitching through tissue or graft. Loop 1455 is coupled to the adjustable loop construct 700 such that it maintains a substantially central location of the passing construct 1450 along the adjustable suture loop 700 (limits sliding of the passing construct 1450 along the saddle portion 704), while allowing the dynamic strand lengths 730b, 730c to slide without inhibiting reduction of the adjustable loop construct 700. The passing suture loop 1455 is coupled to the adjustable loop construct 700 to manage effective passing of the three strand lengths 730a, 730b, 730c through tissue, keeping them aligned relative to each other.

Figure 16B:
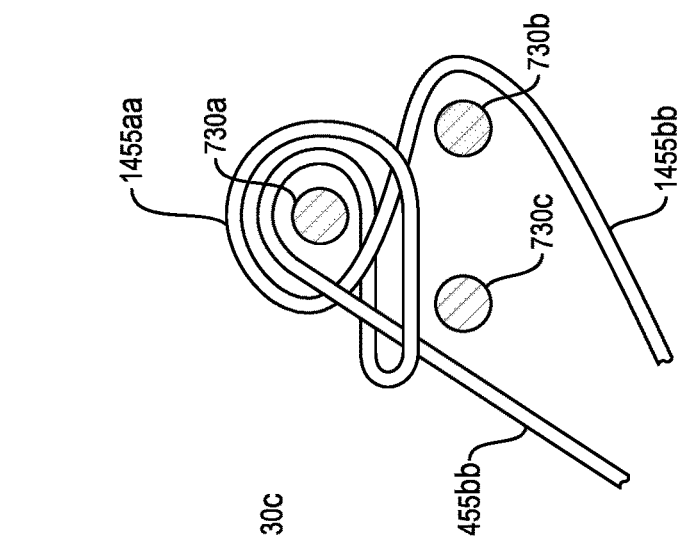
FIGS. 16A-16B illustrate views of a saddle portion of an adjustable loop construct with a passing construct coupled thereto in a split luggage tab configuration, in accordance with this disclosure.
Figure 16A:
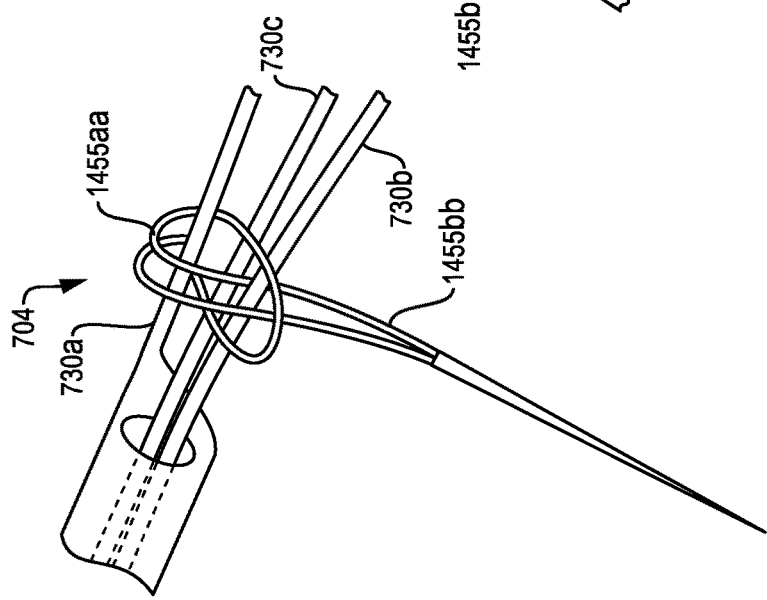

In another configuration, loop 1455 may form a complex loop in the form of a luggage tag loop, around all three strands 730a, 730b, 730c. However, this may cinch around the moving (dynamic) strands 730b, 730c and consequently increases the loop reduction force. A further embodiment is shown in FIG. 16A-16B wherein loop 1455 forms a complex loop in the form of a split luggage tag loop including a first loop 1455aa around the static strand 730a. The second loop 1455bb splits to loop around both sides of the dynamic strands 730b, 730c (seen best in FIG. 16B). This loop however requires a more complicated assembly.

Method of Attaching an Adjustable Loop Construct

A method of attaching an adjustable loop construct 1700 to a graft 1650 is illustrated in FIGS. 17A-17J. Adjustable loop construct 1700 may be similar to adjustable loop constructs (32, 700, 900, 1000) disclosed herein and may be linked to a passing construct 1750 at a linking end 1704 of the adjustable loop construct 1700. Passing construct may be coupled to a linking end 1704 with a complex loop, as disclosed herein. For example, adjustable loop construct may be construct 700 linked to passing construct 1450 at a saddle end 704 with a figure-of-eight loop. However, this method is not limited to construct 700 and construct 1450. The method disclosed couples an adjustable loop construct 1700 to a graft 1650, such that the final stitched graft includes both an adjustable loop construct 1700 and a flexible loop 1755 of a passing construct 1750 stitched therethrough, the flexible loop 1755 linked to, but separately formed from adjustable loop construct 1700. In the final stitched graft, the flexible loop 1755 may define stitches that axially overlap the adjustable loop construct stitches. FIGS. 17A-17J shows a simplified form of an adjustable loop construct 1700, omitting elements such as but not limited to locking passages (such as but not limited to locking passages 710a, 710b) and the individual adjustable loops (such as but not limited to loops 708a, 708b) and a linking end 1704 (such as but not limited to saddle end 704). These details are omitted from the figures to simplify understanding of the figures and thereby method. In addition, this method may couple any of the adjustable loop constructs disclosed herein, or others known in the art, with differing locking passages and adjustable loop configurations to a graft in this manner.

Figure 17A:
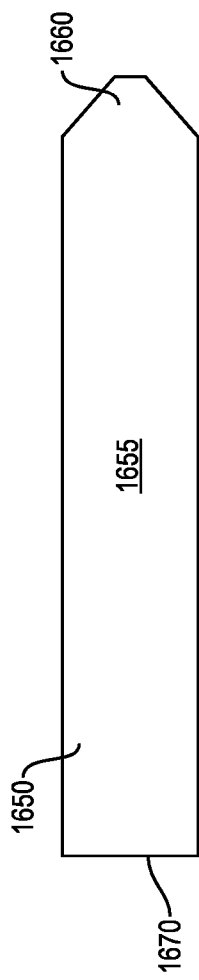

Starting with FIG. 17A, the method may include obtaining and/or obtaining a graft 1650. Graft 1650 may be an elongate body, defining a top side 1655, bottom side 1675, and two opposing ends 1660, 1670. One of the two opposing ends (1670) may be clamped to stabilize the graft 1650 during stitching, and therefore may be defined as a clamped end 1670. The other of the two opposing ends may be the free end 1660. Free end 1660 may be inserted first into a prepared tissue tunnel and may be directly coupled to both the adjustable loop construct and passing construct loop. Free end 1660 may be tapered or bulletized using a scalpel or scissors for easier threading through a prepared bone tunnel. Graft 1650 may be a single solid body, typically harvested from the Quad Tendon. Graft 1650 may include wispy ends. Graft 1650 may be provided as a plurality of elongate strands, typical when harvesting from the hamstring for example. Graft 1650 may be folded over itself to form a target thickness of graft 1650.

Figure 17B:
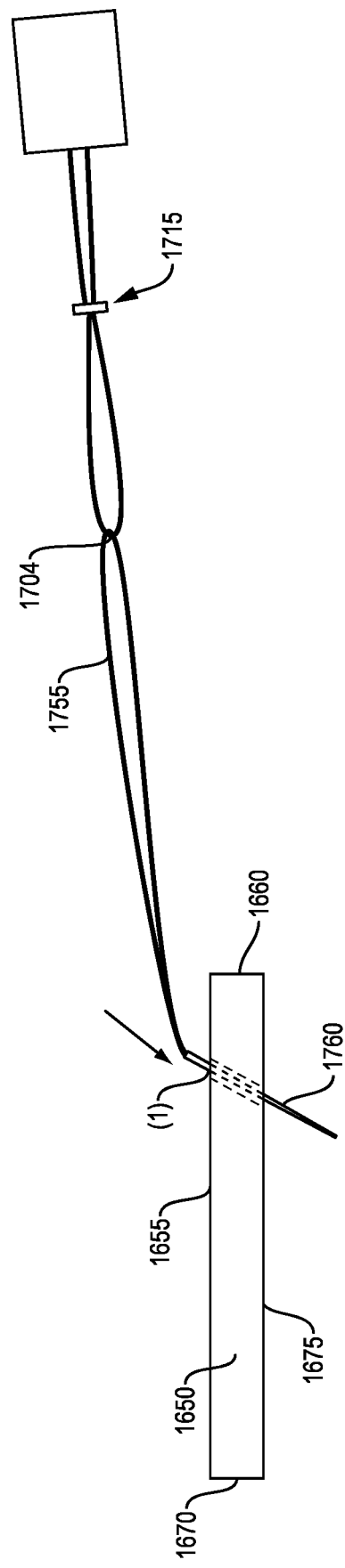

Now turning to FIG. 17B showing a side view of the graft 1650, the method of attaching may include forming and/or obtaining an adjustable loop construct 1700 that may be assembled to a cortical button 1715 at one end and assembled to a flexible loop 1755 of a passing construct at the other end (hereinafter linked end 1704). The flexible loop 1755 may be operatively coupled to a threading member 1760 such as a needle defining, together, the passing construct 1750. Threading member 1760 may pierce the graft top surface 1655 and draw the flexible loop 1755 from the graft top surface 1655 through the thickness of graft 1650 to the lower external surface 1675, at a first location (1), defining a first pass through the graft 1650. First location (1) may be about 1.5 cm-2 cm from terminal edge of free end 1660. In some example methods, flexible loop 1755 may form a complex loop and couple to a plurality of strands (730a, 730b, 730c) along the linked end 1704 that may be similar to saddle end 704. Complex loop is not shown in FIGS. 17B-17J but may be seen in at least FIG. 15 and may be configured to stagger entrance of the plurality of strands (730a, 730b, 730c) through the graft 1650 during this first pass. Complex loop may also maintain a location of the flexible loop within a target zone along the adjustable loop construct 1700. The first pass may be complete when passing construct 1750 is drawn completely through graft 1650, until the entire passing construct 1750 is external to the graft 1650 and the adjustable loop construct 1700 extends through graft 1650 and from both the top surface 1655 and bottom surface 1675 (FIG. 17C). The conclusion of the first pass places the cortical button 1715 adjacent the free end 1660 and top surface 1655 and the linked end 1704 adjacent the bottom surface 1675 (FIG. 17C). This may also preferably place any locking passages external to the graft 1650 adjacent the bottom side 1675. Adjustable loop construct 1700 may include two limbs 1705a, 1705b wrapped around a carrying card or tool 1725 for management thereof. First pass may extend through the graft 1650 at an angle that is neither inclined relative to the longitudinal axis (Y-Y), and therefore neither parallel to nor orthogonal to longitudinal axis (Y-Y) of the graft 1650. Angle may be between 30-60 degrees relative to the longitudinal axis. First pass may extend along and intersect the longitudinal axis. First pass, and all subsequent passes may extend through a midline of the graft 1650, as best possible, given the nature of soft tissue grafts.

Figure 17E:
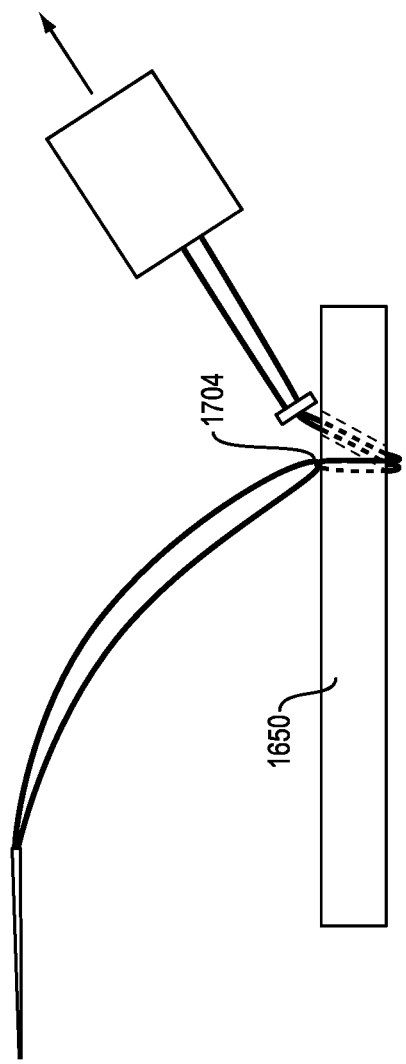

The adjustable loop construct linked end 1704 may then be spread to wrap around both external side surfaces of graft 1650 and flip over the free end 1660, the button 1715 and card or tool 1725 to the top surface 1655 (FIG. 17D). This may place the linked end 1704 between the clamped end 1670 and the first location (1). The adjustable loop construct 1700 may then be reduced via tension on the limbs 1705a, 1705b (which may be coupled to a card or tool 1725). Adjustable loop construct 1700 may be reduced such that the linked end 1704 is circumferentially wrapped around the external surfaces of graft 1650 (FIG. 17E) and button 1715 is adjacent free end 1660. While flipping the linked end 1704, the flexible loop 1755 of passing construct 1750 may be maintained between any locking passages, via the complex loop such as the figure-of-eight loop through the linked end 1704. Adjustable loop construct 1700 may be reduced by drawing the flexible strand through any locking passages of the adjustable loop construct 1700, such that the locking passages circumferentially wrapped around the external surfaces of graft 1650 (FIG. 17E). Reducing the construct 1700 may place the locking passages substantially external to the graft and not within the graft, which may cinch the locking passages and frustrate loop reduction.

Figure 17F:
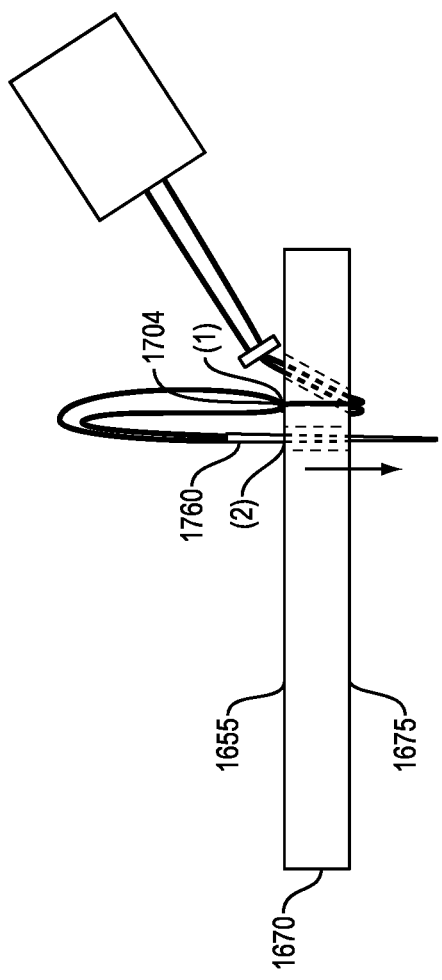
Figure 17G:
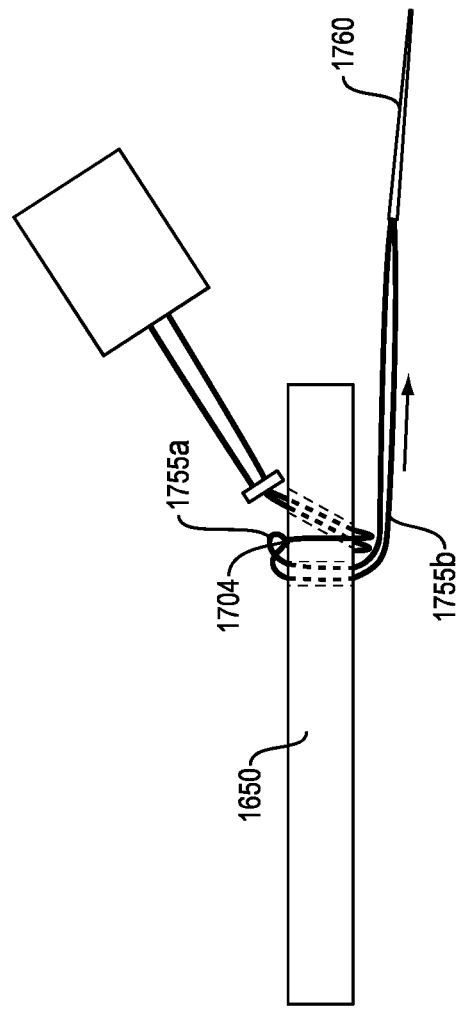

Turning now to FIG. 17F, threading member 1760 may be passed again (second pass) from the graft top surface 1655 to the bottom surface 1675, at a second location (2), directly adjacent to linked end 1704 (FIG. 17F). This locks the location of linked end 1704 along the graft 1650 and prevents the linked end 1704 from sliding along the graft 1650. Second location (2) may be approximately coincident with linked end 1704, and between the clamped end 1670 and first location (1). The adjustable loop construct 1700 in now fixedly attached to the graft 1650. The second pass may be orthogonal to the graft longitudinal axis (Y-Y) and may define the furthest-most pass from the free end 1660. At the end of the second pass a portion of flexible loop 1755 may extend through the graft 1650. At the end of the second pass (FIG. 17G) a first loop 1755a of a complex loop of flexible loop 1755 may be retained on top surface 1655 while second loop 1755b may extend through graft 1650.

Figure 17H:
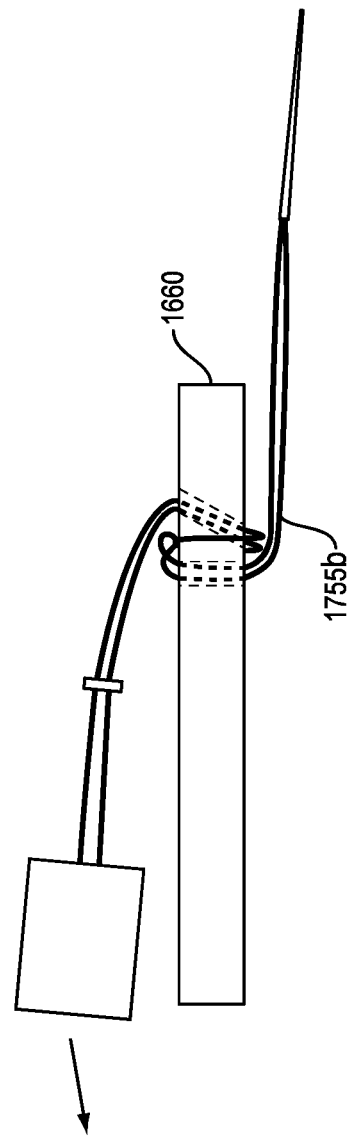
Figure 17I:
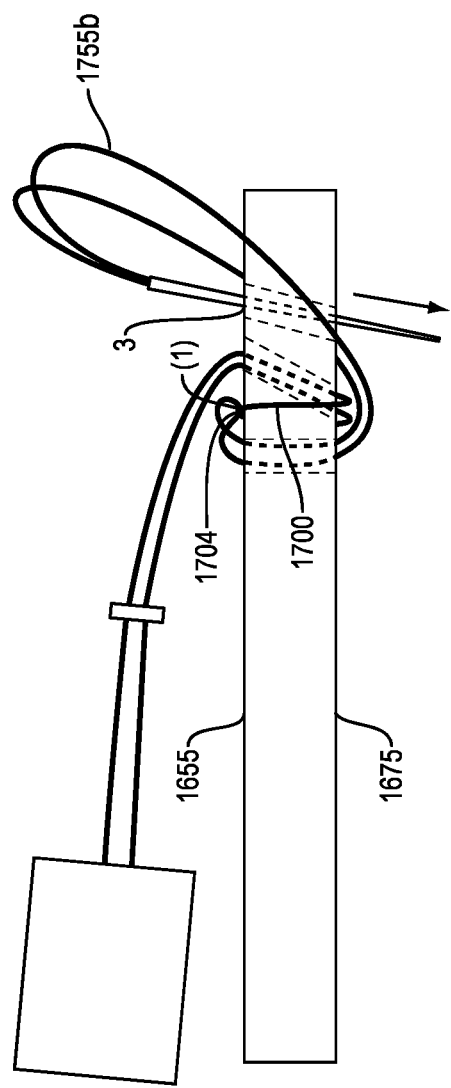

The flexible loop 1755 may now form a running whipstitch along graft 1650, progressively moving towards the free end 1660, the running whipstitch preferably including at least two whipstitch passes (a third and a fourth pass of the attachment method) through the graft 1650. This running whipstitch forms a plurality of axially spaced circumferential wraps around the graft free end 1660. Tensioning these plurality of axially spaced circumferential wraps forms the graft free end 1660 into a more cylindrical shape, for easier passing through the prepared bone tunnel. Tensioning on these whipstitches may further taper the graft free end 1660, for easier passing through the prepared bone tunnel. This running whipstitch may include at least two passes, and acts to mitigate attachment rip-stopping (adjustable loop construct 1700 and flexible loop 1755 from cheese-wiring out of graft). Whipstitches run progressively towards the free end 1660. Whipstitches may be formed by looping the flexible loop 1755 (which may be second loop 1755*b*) around from the bottom surface 1675 and end 1660 to place the threading member 1760 on the top surface (FIG. 17H and FIG. 17I). Threading member 1760 may then passe from the top surface 1655 to the bottom surface 1675 again. This may be at a location (3) between free end 1660 and location (1). This may circumferentially wrap the flexible loop 1755 (1755*b*) around the graft 1650, over and across the adjustable loop 1700 that is wrapped around the graft external side surfaces and the linked end 1704.

Figure 17J:
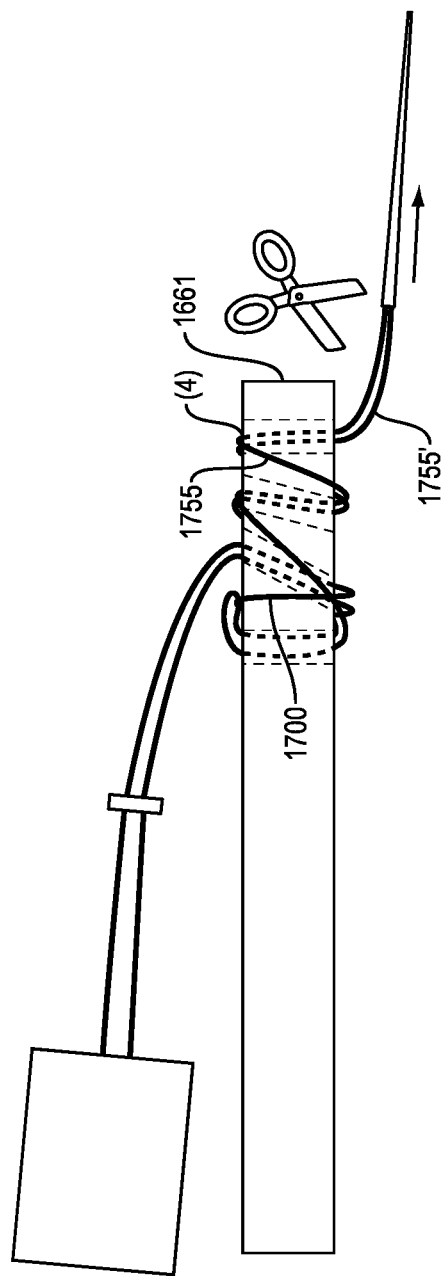

The steps shown in FIG. 17H-17I may be repeated to form a second whipstitch of the running whipstitch, shown in FIG. 17J. Flexible loop 1755 may be wrapped around the graft 1650 and over the free end 1660 to place the threading member 1760 on the top surface 1655. Threading member 1760 may then pierce the graft and pass through from the top surface 1655 to the bottom surface 1675 at a location between location (4) and free end 1660. This may be repeated until the whipstitch passes reach the terminal edge 1661 of the free end 1660. Loop 1755 may then be tied in a knot and cinched tightly to further taper tapered free end 1660. The threading member 1760 may then be removed, leaving a trimmed loop 1755' available (FIG. 17J).

Graft 1650 coupled to adjustable loop construct 1700 and trimmed loop 1755' (trimmed from threading member 1760) may then be threaded through a prepared bone tunnel (not shown). Trimmed loop 1755' (FIG. 17J) may be sufficiently long to couple to a tool to draw graft 1650 into and along prepared bone tunnel. Trimmed loop 1755' therefore has a length, as provided or obtained sufficient to form at least two whipstitch passes through a graft, leaving sufficient length to be drawn along prepared bone tunnel. Drawing on the trimmed loop 1755' is preferable over drawing with the adjustable construct 1700 to avoid the graft free end 1660 from folding over itself while sliding through prepared bone tunnel. Drawing on the adjustable construct 1700 only may form a fold adjacent second location (2).

Turning now to a more specific example, a method of attaching may include forming or obtaining adjustable loop construct 700 assembled with a cortical button 750 at one end and coupled to a passing construct 1450 at saddle end 704. Needle 1460 may pierce the graft top surface 1655 and draw the loop 1455 of passing construct 1450 from the graft top surface 1655 through the thickness of graft 1650 to the lower external surface 1675, at a first location (1), defining a first pass. First location may be about 1.5 cm-2 cm from terminal edge 1661 of free end 1660. In some example methods, flexible loop 1455 may form a complex loop and couple to a plurality of strands (730*a*, 730*b*, 730*c*) along the saddle end 704. Complex loop may be configured to stagger entrance of the plurality of strands (730*a*, 730*b*, 730*c*) through the graft 1650 during this first pass. Complex loop may be a figure-of eight loop, with a first loop 1455*a* looped about static strand 730*a*, and a second loop 1455*b* looped around strands 730*b*, 730*c*. The first pass may be complete when passing construct 1450 is drawn completely through graft 1650, until the entire passing construct 1450 is external to the graft 1650 and the adjustable loop construct 700 extends through graft 1650 and from both the top surface 1655 and bottom surface 1675. The conclusion of the first pass places the cortical button 750 adjacent the top surface 1655 and the saddle end 704 adjacent the bottom surface 1675. Adjustable loop construct 700 may include two limbs (705*a*, 705*b*) wrapped around a carrying card or tool 1725 for management thereof. First pass may extend through the graft 1655 at an angle that is inclined relative to a longitudinal axis (L-L) of the graft 1650. Angle may be between 30-60 degrees relative to the longitudinal axis. First pass may extend along and intersect the longitudinal axis. First pass may be oriented substantially along a midline of the graft 1650, as best possible, given the nature of soft tissue grafts.

Saddle end 704 may then be spread to wrap around both sides of graft 1650 and flip over the free end 1660, the button 750 and card or tool 1725 to the top surface 1655. This may place the saddle end 704 between the clamped end and the first location (1) on the top side 1655. The adjustable loop construct 700 may then be reduced via tension on the limbs 705*a*, 705*b* (which may be coupled to a card or tool 1725. Adjustable loop construct 700 may be reduced such that the saddle end 704 is circumferentially wrapped around the graft 1650 and button 750 is adjacent free end 1660. While flipping the saddle end 704, the passing construct 1450 may be maintained between locking passages (710*a*, 710*b*), via the complex loop such as the figure-of-eight loop through the saddle end 704.

Needle 1460 may be passed again (second pass) from the graft top surface 1655 to the bottom surface 1675, at a second location (2), directly adjacent to saddle end 704. This locks the location of saddle end 704 along the graft 1650 and prevents the saddle end 704 from sliding along the graft 1650. Second location (2) may be approximately coincident with saddle end 704, and between the clamped end 1670 and first insertion location (1). The adjustable loop construct 700 in now fixedly attached to the graft 1650. The second pass may be approximately orthogonal to the graft longitudinal axis and may define the furthest-most pass from the free end 1660. At the end of the second pass a portion of flexible loop 1455 may extend through the graft 1650. At the end of the second pass a first loop 1455*a* of the complex loop of flexible loop 1455 may be retained on top surface 1655 while second loop 1455*b* may extend through graft 1650.

The flexible loop 1455 may now form a running whipstitch that progressively stitches towards the free end 1660, the running whipstitch preferably including at least two whipstitch passes (a third and a fourth pass of the attachment method) through the graft 1650. This running whipstitch forms a plurality of axially spaced circumferential wraps around the graft free end 1660. Tensioning these plurality of axially spaced circumferential wraps forms the graft free end 1660 into a more cylindrical shape, for easier passing through the prepared bone tunnel. Tensioning on these whipstitches may further taper the graft free end 1660, for easier passing through the prepared bone tunnel. This running whipstitch may include at least two passes, and acts to mitigate attachment rip-stopping (adjustable loop construct 700 and flexible loop 1455 from cheese-wiring out of graft). Whipstitches run progressively towards the free end 1660. Whipstitches may be formed by looping the second loop 1455*b* around from the bottom surface 1675 and graft end 1660 to place the needle 1460 on the top surface. Needle 1460 then passes through from the top surface 1655 to the bottom surface 1675. This may be at a location (3) between free end 1660 and insertion location (1). This may circumferentially wrap the second loop 1455*b* around the graft 1650, over and across the adjustable loop saddle end 704. This may circumferentially wrap the second loop 1455*b* around the graft 1650, over and across the locking passages 710*a*, 710*b* such that upon tensioning this, the locking passages 710*a*, 710*b* may no longer be adjustable.

A second whipstitch may be formed by looping the second loop 1455*b* again around from the bottom surface 1675 and end 1660 to place the needle 1460 on the top surface. Needle 1460 then passes again through from the top surface 1655 to the bottom surface 1675. This may be at a location between free end 1660 and insertion location (3). This may be repeated until the whipstitch passes reach the terminal edge of the free end 1660. Second loop 1455*b* may then be tied in a knot 1810 and cinched tightly to further taper tapered free end 1660. The needle 1460 may then be removed, leaving a length of second loop 1455*b* available (that may no longer be a loop.) Graft 1650 coupled to adjustable loop construct 700 and second loop 1455*b*' (trimmed from needle 1460) may then be threaded through a prepared bone tunnel (not shown).

Figure 18A:
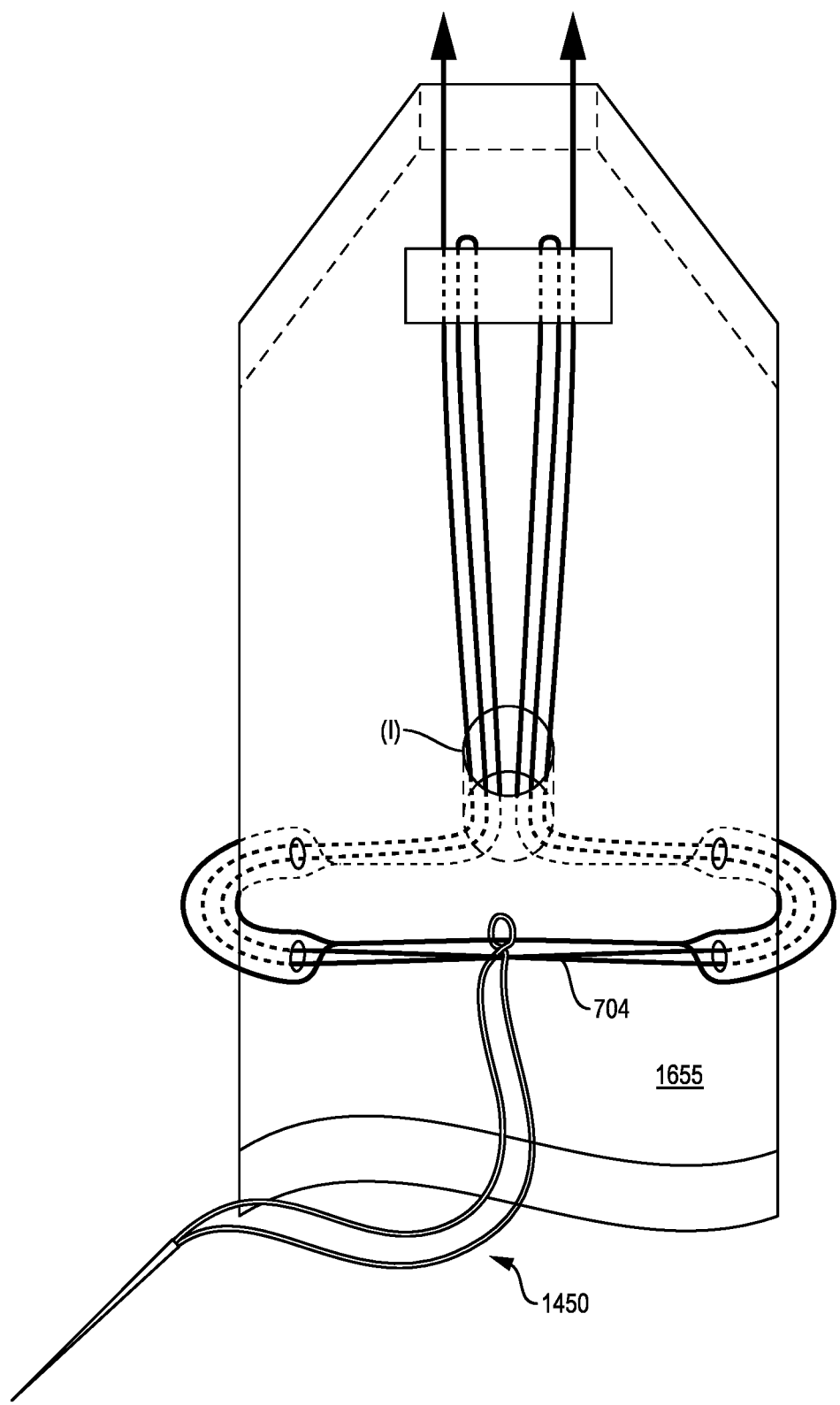
FIG. 18A illustrates a top view of a stitched arrangement after the first pass (FIG. 17E) according the method disclosed in FIG. 17A-17J.
Figure 18B:
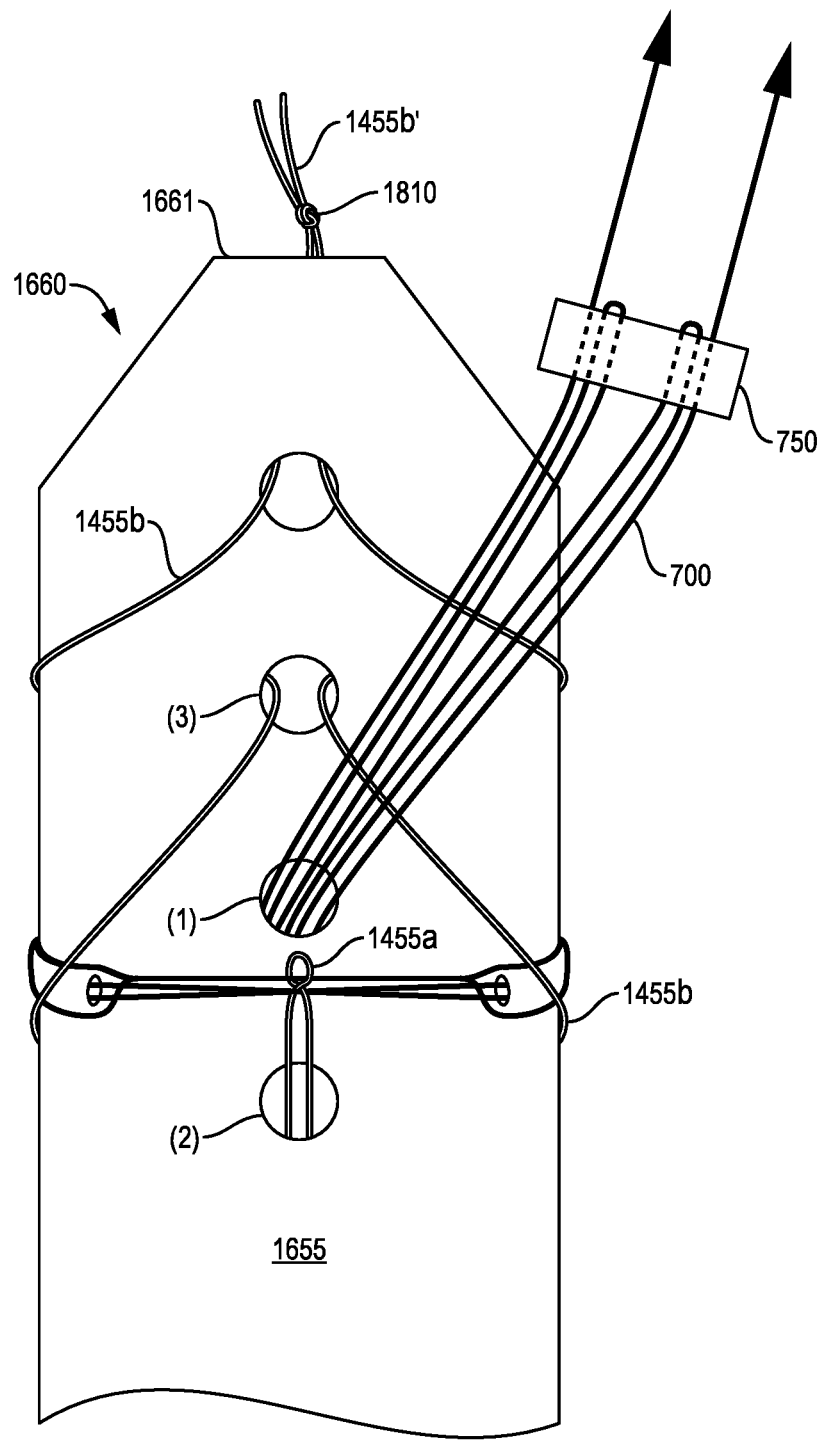
FIG. 18B illustrates a top view of a final stitched arrangement according the method disclosed in FIG. 17A-17J.

FIG. 18A illustrates a top down view of the adjustable loop construct 700 stitched through graft 1650, after the first pass and before the second pass, similar to arrangement shown in FIG. 17E. FIG. 18B illustrates a top down view of the adjustable loop construct 700 and flexible loop 1455 stitched through graft 1650, in the final stitched configuration. FIG. 18B also shows the circumferential wraps and tapering of the free end 1660. Knot 1855 is shown in second loop 1455*b* with trimmed second loop 1455*b*' extending therefrom.

Reduction Bar

FIGS. 11A-13D illustrate various features of a reduction bar 1100 and an associated method of use. Reduction bar 1100 may provide a plurality of functions during a tissue repair. Reduction bar 1100 may be assembled to an adjustable suspensory fixation system and used as a handle or tool that applies tension to adjustable loops of the fixation system to place the graft in the target location. Reduction bar 1100 may also be provided or obtained with the suspensory fixation system preassembled thereto and therefore could equally be called a fixation system storage tool.

Suspensory fixation systems, such as system 280 shown in FIG. 3A include multiple loops of a flexible strand 30, which if provided in loose form may be difficult to keep track of and prone to strand entanglement or errors while coupling to the graft. Reduction bar 1100 may include retaining and storing means including cavities, slots, cleats, channels and spools arranged along the reduction bar 1100, for housing or retaining portions of the suspensory fixation system. Other example fixation systems that may be assembled to this reduction bar 1100, are disclosed herein, as well as in commonly owned PCT patent application number PCT/US20/038401 filed Jun. 18, 2020, titled "METHODS AND DEVICES FOR TISSUE GRAFT FIXATION" commonly owned and herein incorporated by reference in its entirety.

These storing means may retain and manage components of the suspensory fixation system such that they are on an external surface of bar 1100 and selectively removeable from the bar 1100 in stages, according to the stages of operation of the tissue repair. Reduction Bar 1100 may therefore not only store a suspensory fixation system but also arrange the suspensory fixation system to guide the staged release thereof, according to the preferred stages of the procedure.

More specifically, these storing means may arrange components of a suspension fixation system that may include an adjustable loop construct (32), passing construct (300) and tissue anchor (100, 200) around the reduction bar 1100 such that release of these components is staged to improve management of the suspensory fixation system during the tissue repair and limit entanglements and confusion. With reference to FIGS. 3A-3E, these storing means may arrange the adjustable loop construct 32, passing construct 300 and tissue anchor 100, 200 around the reduction bar 1100 such that the passing construct 300 may be released first, the passing construct 300 preassembled to the free limb 33*b* and free adjustable loop 35*b*. The free limb 33*b* and free adjustable loop 35*b* may then be removed from the bar 1100. The remains of the suspensory fixation system 280 may be left retained by the bar 1100, while the passing construct 300, free limb 33*b* and free adjustable loop 35*b* are coupled to the graft (FIG. 3A).

Figure 11A:
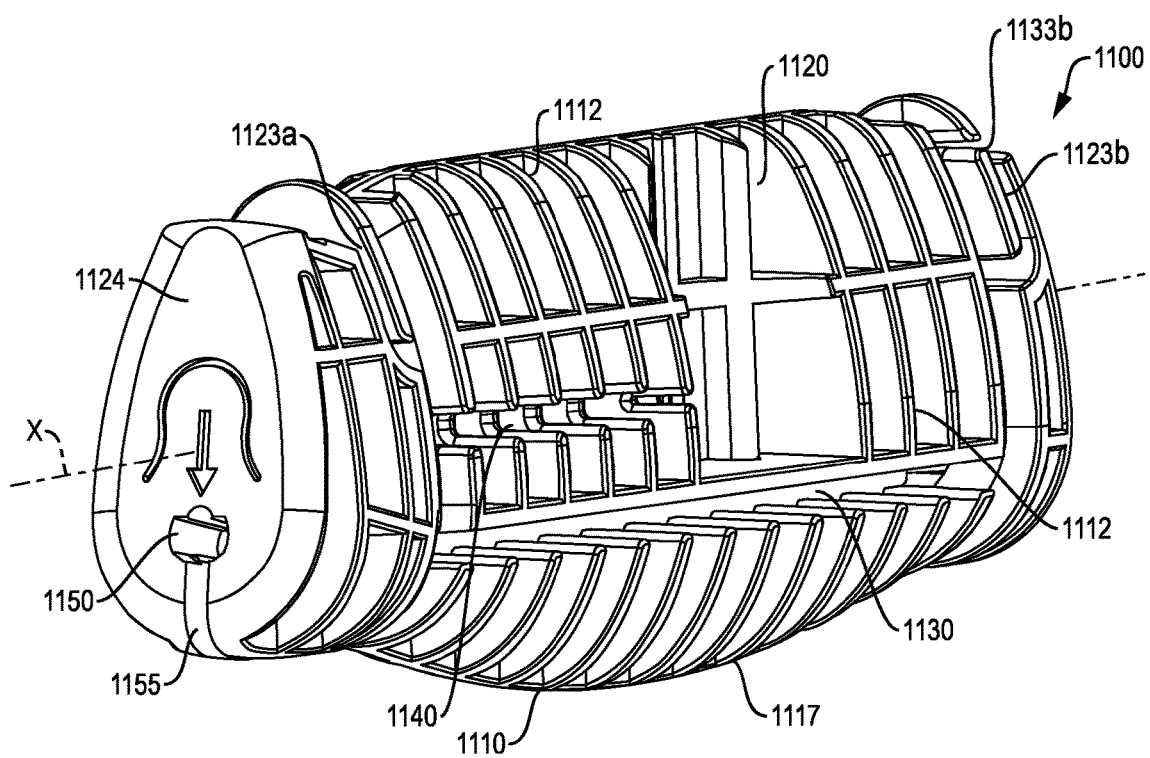
FIG. 11A illustrates a perspective view of a reduction bar in accordance with this disclosure.
Figure 11B:
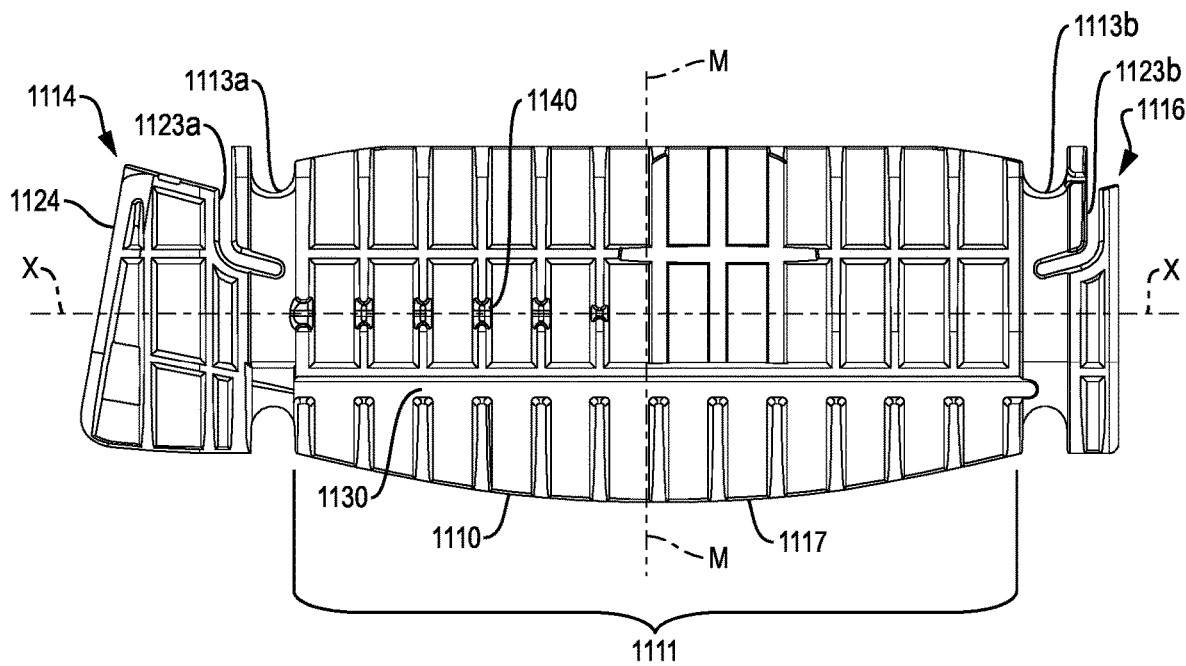
FIG. 11B illustrates a front side view of the reduction bar in accordance with this disclosure.
Figure 11C:
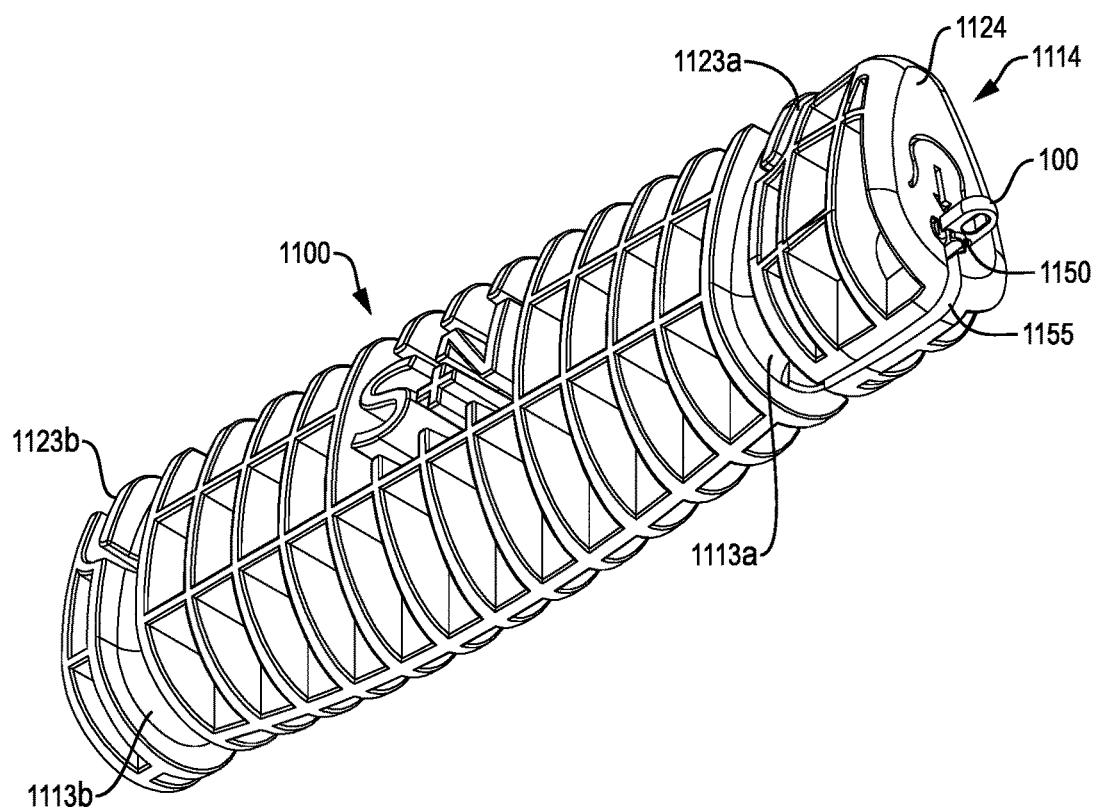
FIG. 11C illustrates another view of the reduction bar with a button assembled thereto, in accordance with this disclosure.
Figure 11D:
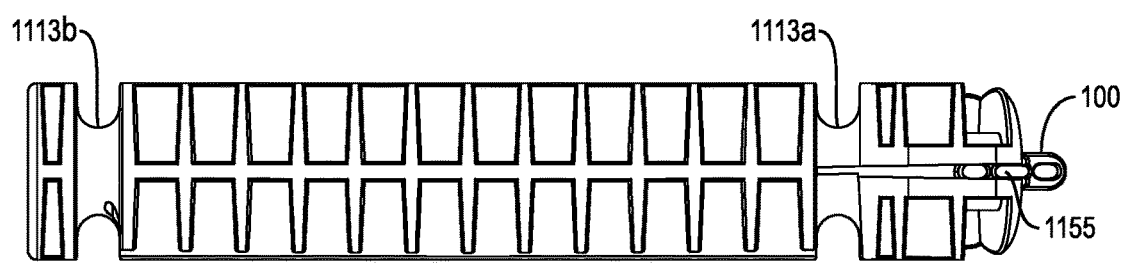
FIG. 11D illustrates a bottom view of the reduction bar with a button anchor assembled thereto, in accordance with this disclosure.
Figure 11E:
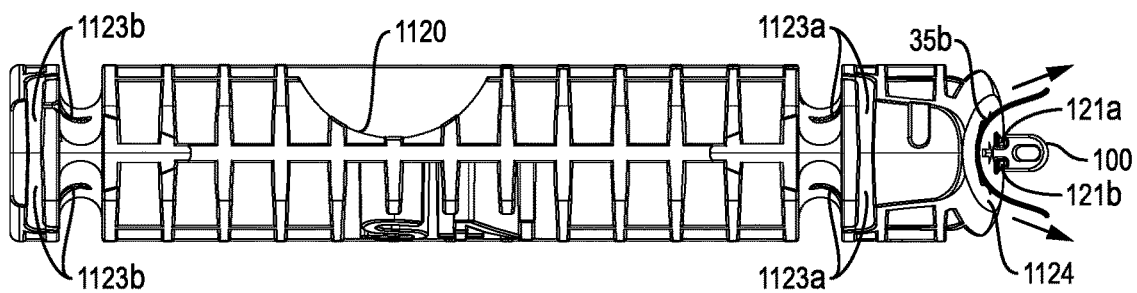
FIG. 11E illustrates a top view of the reduction bar with a button anchor assembled thereto, in accordance with this disclosure.

Additionally, the reduction bar 1100 may operate as a tool that guides closing of an open adjustable loop construct such as suspensory fixation system 280. For example, the anchor (100, 200) may be provided stored within the bar 1100 in an orientation that exposes the slotted apertures 120*a*, 120*b* (FIG. 11C-11E). The slotted apertures 120*a*, 120*b* may align with a guide surface of the reduction bar 1100, to align and guide the free adjustable loop 35*b* into the slotted apertures 120*a*, 120*b*.

Additionally, the reduction bar 1100 may operate as a handle while reducing the adjustable loop construct 32, and thereby alleviate forces on the surgeon's hand. Reduction bar 1100 may include a means of operatively coupling to looped limb ends 33*a*, 33*b* of the adjustable loop construct 32 for example, placing the suspensory fixation system 280 in a reducing configuration. The bar 1100 may then be rocked and rotated while applying tension to the ends 33*a*, 33*b*, to reduce the adjustable loop construct size and thereby draw the tissue, graft, or tissue anchor towards the tissue anchor (100, 200).

As such, reduction bar 1100 is a multi-functional handle body, configured to store a suspensory fixation system that may include at least one of an adjustable loop construct, a tissue anchor, and a passing construct. Reduction bar 1100 may also provide a means of guiding assembly of an open loop adjustable construct to the tissue anchor. Reduction bar 1100 may be provided assembled with the suspensory fixation system, to stage the release of components of the system in accordance with the tissue repair. Reduction bar 1100 may also reassemble with the adjustable loop construct, in a different arrangement to the preassembled arrangement to reduce/adjust the adjustable loop construct.

FIGS. 11A-11E illustrate various features of reduction bar 1100, with a suspension fixation system removed. Starting with FIGS. 11A and 11B, reduction bar 1100 may generally be a unibody, sized to fit within a surgeon's hand and be comfortable while tensioning and reducing the adjustable loop construct. Reduction bar 1100 may define an elongate body, defining a longitudinal axis X-X and an oval or oblong cross section. Bar 1100 may have a more bulbous, larger cross section along a lower side 1117, configured to sit within a user's curled fingers. Bar lower side 1117 may also define an arced or convex curved surface 1110, curved along the longitudinal axis X-X such that the handle 1100 has thickest cross section close to a midline M-M of handle 1100. Elongate convex curved surface 1110 and bulbous lower side 1117 together are shaped to rests within a surgeon's fingers while applying tension on the adjustable loop construct.

Bar 1100 has a medial length portion 1111, with circumferential spools 1113a, 1113b at either end thereof. Bar 1100 includes a first lateral end 1114 extending from spool 1113a that has a first lateral end surface 1124 that may be planar. A second opposing lateral end 1116 extends from spool 1113b. Each spool may be intersected (one each) by a notch 1123a, 1123b. Each notch 1123a, 1123b may be curved and may be an "L" shape, or reverse "L" shape. Each notch 1123a, 1123b extends through a thickness of the bar 1100, best shown in FIG. 11E. Bar End 1114 may be different to bar end 1116. Bar end 1114 may extend further along the longitudinal axis X-X from the medial portion 1111. Therefore bar 1100 may be an asymmetrical body about a plane through the midline M-M. Bar end 1114 is sized to include a slot 1150 for housing a portion of a tissue anchor. Bar end 1114 includes channel 1155 extending from slot 1150 for housing a portion a flexible strand coupled to the anchor.

Bar 1100 may define a plurality of circumferentially extending ribs 1112 that may add structural integrity to the bar 1100 while accommodating manufacturing processes and reducing material use. At least some of the ribs 1112 may be non-continuous, defining gaps along the medial length portion 1111, such as relief 1120, channel 1130 and retention channel 1140. These gaps may provide at least some of the storing means for portions of the suspensory fixation system including the adjustable loop construct and passing construct, disclosed in more detail hereafter.

FIGS. 11C-11E illustrates various views of bar 1100 with an example button assembled thereto. FIG. 11C illustrates the back side of bar 1100, that may be free of any retaining slots or channels along the median portion 1111. Slot 1150 is configured to house a portion of button, such as button 100, 200. FIG. 11D illustrates button 100, 200 housed within slot 1150. The channel 1155 is continuous with and extends from the slot 1150 and is also continuous with spool 1113a, such that a portion of the adjustable loop construct (shown in later figures) coupled to the button may extend from within the slot 1150, along channel 1155 and into and around spool 1113a (FIG. 12C).

Slot 1150 may house button 100 to expose a portion thereof including lateral openings 121a, 121b, seen best in FIG. 11E. Planar surface 1124 may be orientated at a non-orthogonal angle to longitudinal axis X-X and may provide a guiding surface when assembling a free adjustable loop end 35b of an open adjustable loop construct to cortical button (a small portion of free adjustable loop end 35b is shown adjacent surface 1124) As such sliding free adjustable loop end 35b along surface 1124 (see arrow) may thread the adjustable loop end 35b through the lateral slots 121a, 121b and into the slotted apertures 120a, 120b to close the open adjustable loop construct 32 (FIG. 3C, 3D). This preferably occurs after threading the free loop end 35b through a graft, as disclosed herein.

Figure 12A:
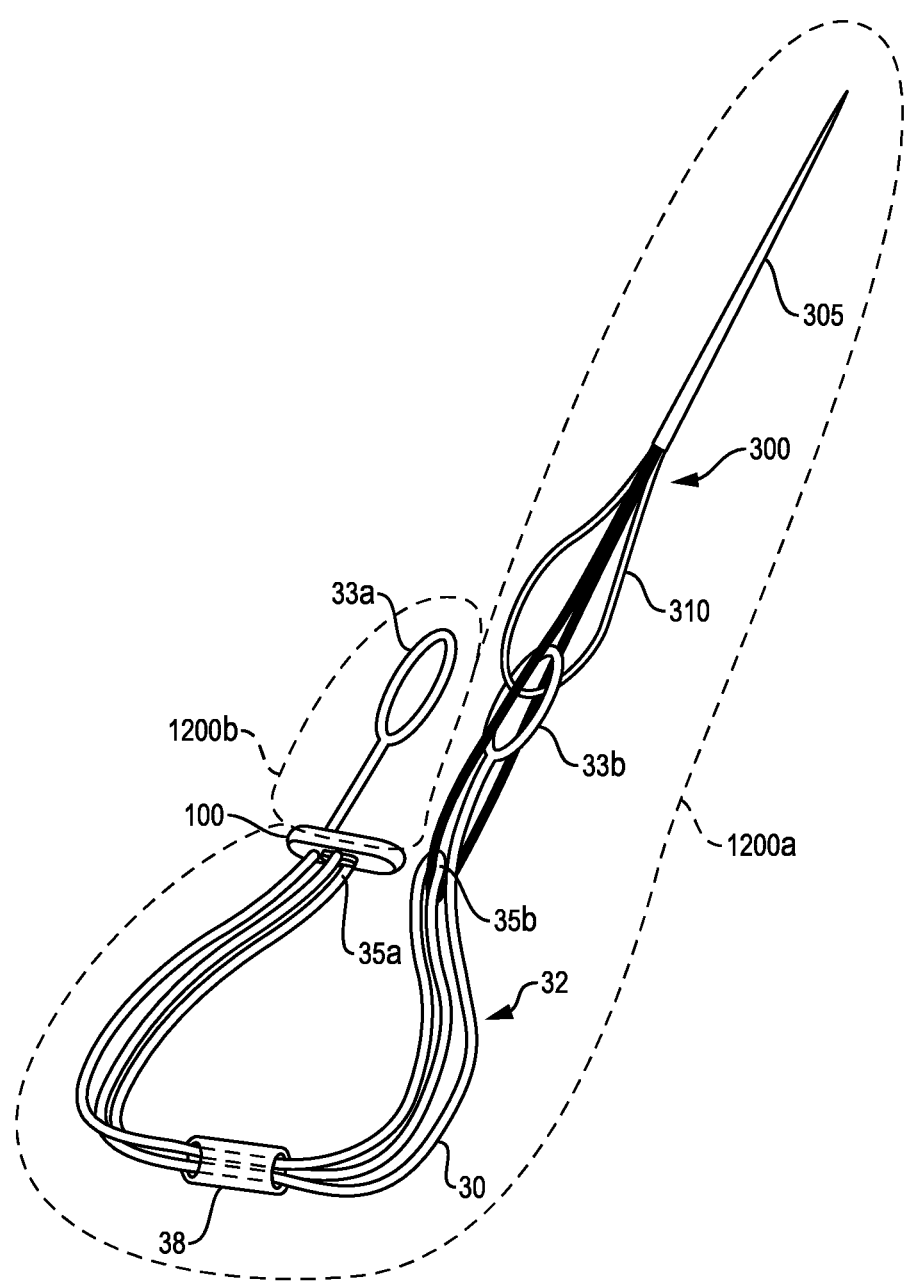
FIG. 12A illustrates a suspension fixation system, and portions thereof, in accordance with this disclosure.

FIG. 12A illustrates the suspension fixation system 280. This includes a button 100 (illustrated in simpler form), and adjustable loop construct 32. For understanding of assembly of the suspension fixation system 280 to the reduction bar 1100, FIG. 12A illustrates an imaginary split of the suspension fixation system 280 into portions 1200a and 1200b. Portion 1200a, as indicated on the figure may include the passing construct 300, (threading element 305 and passing loop 310) the free adjustable loop end 35b, the free looped end 33b, the locking passage 38. Portion 1200a may also include some of the flexible strand 30 that forms the portion of the assembled loop end 35a that extends directly between the locking passage 38 and anchor 100. Portion 1200a may also include all strands 30 that extend directly between anchor 100 and passage 38. As such is may include strand length portions of first looped end 33a and limb 35b that are directly between the button 100 and locking passage 38. Portion 1200b as indicated on the figure may include the anchor 100, assembled to the assembled loop end 35a and the looped end 33a.

Figure 12B:
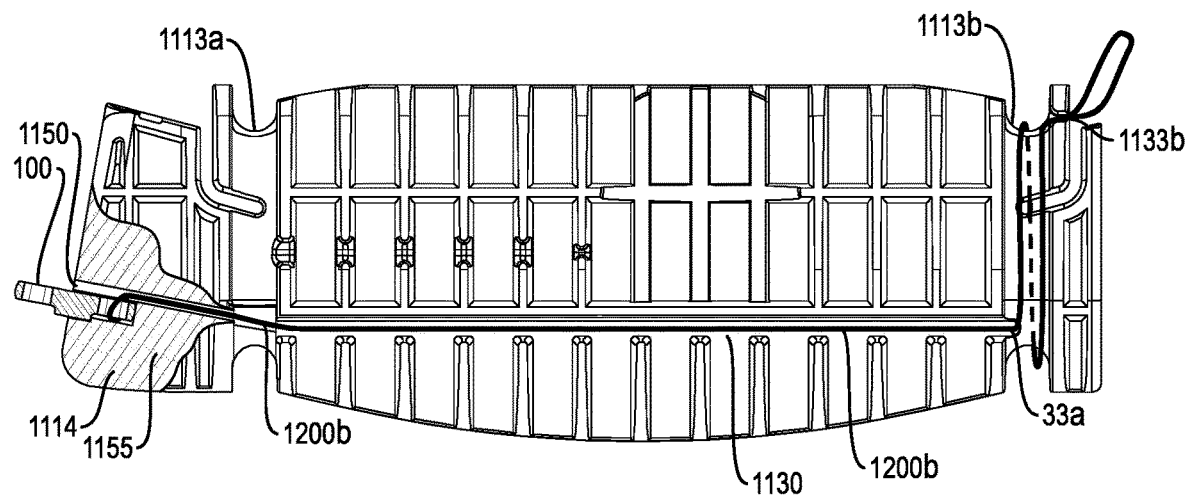
FIGS. 12B and 12C illustrate portions of the suspension fixation system assembled to the reduction bar, in accordance with this disclosure.
Figure 12C:
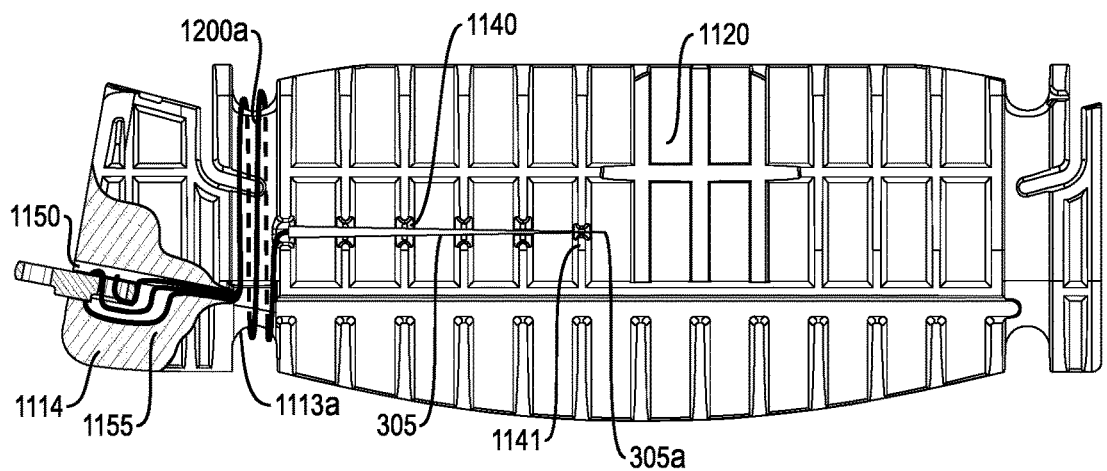

FIGS. 12B and 12C illustrate (in combination) how the bar 1100 and a suspensory fixation system may be provided or obtained in a preassembled configuration. In the example, suspensory fixation system 280 is assembled to the bar 1100, and reference made to FIGS. 3A-3E and FIG. 12A. Other suspensory fixation systems may assemble using similar philosophies, however. Both FIGS. 12B and 12C are to be viewed in combination. Stated another way, as provided both portions 1200a and 1200b may be assembled to the reduction bar 1100. FIG. 12B illustrates assembly of portion 1200b only with the remainder of the system 280 (portion 1200a) shown assembled in FIG. 12C. Portion 1200a is not shown in FIG. 12B for clarity of understanding. Similarly, only portion 1200a is shown in FIG. 12C, with portion 1200b removed from the figure for simplification of explanation only. As packaged the bar 1100 is pre-assembled to both portions 1200a and 1200b, and both FIGS. 12B and 12C should be viewed in combination to view the preassembled configuration.

Starting with FIG. 12B, a front side of bar 1100 is shown, with a portion of the front half of end 1114 removed for improved understanding of the strand routing. Suspensory fixation construct 280 may be provided in the pre-assembled configuration, with a tissue anchor, such as button 100 nested within slot 1150. This is also shown in at least FIGS. 11C, 11D and 11E. Portion 1200b including looped end 33a may extend recessed within end 1114, along channel 1155, across spool 1113a and into and along channel 1130 towards spool 1113b. Looped end 33a may then wrap around an outermost circumferential surface of spool 1113b for a plurality of wraps and then through cleat 1133b, to secure it in place and prevent uncoiling of looped end 33a. Channel 1130 may be defined by an interruption in the circumferential ribs 1112 around bar 1100. Channel 1130 may extend parallel to longitudinal axis X-X. Channel 1130 may have openings at both spool 1113a and spool 1113b, such that looped end 33a is assembled substantially recessed within channel 1155 and channel 1130 in the assembled configuration. Spools 1113a and 1113b may extend from and be continuous with ends of channel 1130.

FIG. 12C illustrates the routing of portion 1200a. Again, FIG. 12C is illustrated with a portion of the front half of end 1114 removed for improved understanding of the strand routing. The multiple lengths of flexible strand 30 may extend from anchor 100, along channel 1155 and wraps around spool 1113a. Locking passage 38, adjustable looped end 35b and looped end 35b may all wrap around an outermost circumference of spool 1113a (represented in the figure in simplified form to simplify the figure). In addition, flexible loop 310 may also wrap around spool 1113a. Threading member 305 may extend along retention channel 1140. Retention channel 1140 is defined by an interruption in the circumferential ribs 1112, the interruption defining a retention channel width. Retention channel may loosely house threading member 305, except for a central most end of retention channel 1140, defined by end of circumferential ribs that form a narrowed width 1141, spaced to pinch a threading member tip 305a. Retention channel 1140 may be continuous with spool 1113a. Threading member 305 may be oriented parallel to longitudinal axis X-X and may be positively retained at end 1141. Threading member may be a tube, needle or thick portion of a flexible material. Channel 1140 may be continuous with relief or cavity 1120. Threading member tip 305a may extend into relief 1120. Relief 1120 may be deeper than channel 1140 (best seen in FIG. 11E), allowing a user to place a finger or tool within relief 1120 and grasp threading element tip 305a. Threading member tip 305a may be accessible from or extend into relief 1120, relief 1120 defining a cavity within the reduction bar 1100 that allows a surgeon to access and remove the threading member 305 from the reduction bar 1100.

A method of tissue repair may therefore start with the obtaining bar 1100, pre-assembled with the fixation system 280, including both portions 1200a and 1200b, as shown in FIGS. 12B and 12C in combination. A surgeon may first remove portion 1200a. This includes first removing the threading member 305 from the channel 1140 by placing a finger or tool in the relief 1120 and engaging a tip 305a of threading member 305. Once removed, a portion of the adjustable loop construct 280 may then be uncoiled from spool 1113a. This may include uncoiling a flexible loop 310, an adjustable free looped end 35b, a looped end 33b and at least one locking passage 38 from the spool 1113a. With portion 1200b still assembled to bar 1100, threading member 305 may be then inserted through a body (tissue/graft or tissue anchor) to couple the suspensory fixation system 280 thereto. While inserting the threading member 305 through the body, the cortical button (100, 200) may remain within slot 1150. While inserting the threading member 305 through the body, a looped end 33a may remain coiled around spool 1113b. Inserting the threading member 305 may include inserting the threading member 305 through a bone hole 6a which first draws looped end 33b through the hole 6a, and then draws the adjustable loop 35b through the bone hole 6a.

Once coupled to the body, bar 1100 may also serves as a tool to ease coupling the free adjustable loop end 33b and free looped end 35b to button 100. After the suspensory fixation system 280 is coupled to the body, the threading member 310 may be inserted through an aperture (135b) of the button 100 disposed adjacent surface 1124 of bar 1100, to draw looped end 33b therethrough, while button 100 is held within bar slot 1150. As shown in at least FIG. 11C, 11D, button 100 is orientated by slot 1150 to expose lateral slots 121a, 121b and aperture 135b. Lateral slots 121a, 121b may align with planar surface 1124. End 1114 and slot 1150 is therefore deep enough to house the button 100 in this orientation while aligning the lateral slots 121a, 121b with the planar surface 1124. Free looped end 35b may slidingly engage with surface 1124 and be drawn towards the slotted apertures 121a, 121b, to thread the adjustable loop 35b over the top side 108 of button 100 and into slotted apertures 121a, 121b, illustrated in FIG. 11E. Surface 1124 may be coincident with a portion of lateral slots 121a, 121b.

Continuing with the example method, the entire suspensory fixation construct 280 may now be removed from the reduction bar 1100, including now removing portion 1200b, before being reassembled into a reducing configuration. In this reducing configuration, reduction bar 1100 may be a tool to impart tension on the system 280 and reduce the adjustable loop construct 32. This tension may also knotlessly lock any locking passages of the system 280.

To assemble in the reducing configuration, looped ends 33a and 33b may slide, one each, into and along notches 1123a, 1123b to lie around a segment of their corresponding spools 1113a, 1113b. Notches 1123a, 1123b define a reduced perimeter relative to the outermost spools 1113a, 1113b, having a secondary surface or cut-through that looped ends 33a, 33b may lie in, illustrated best in FIG. 13A-13B. Looped ends 33a, 33b may extend quite a long distance from button 100, this long distance being cumbersome. The act of reducing the system 280 may increase this distance further. Bar 1100 may preferably be first rotated (indicated as step 1 in FIG. 13D) around its longitudinal axis, to shorten the length of ends 33a, 33b before and as the adjustable loop construct reduces. Reducing the adjustable loop construct 32 and rotating the bar 1100 may be performed sequentially and repeatedly. For example, the bar 1100 may first be rotated to wrap a portion of the ends 33a, 33b around spool 1113a, 1113b, then tension (indicated by arrow step 2) may be applied to reduce the adjustable loop size (which lengthens ends 33a, 33b). Then the bar 1100 may be rotated again to further wrap ends 33a, 33b around the corresponding spool 1113a, 1113b), to reduce the distance between the bar 1100 and button 100.

Figure 13A:
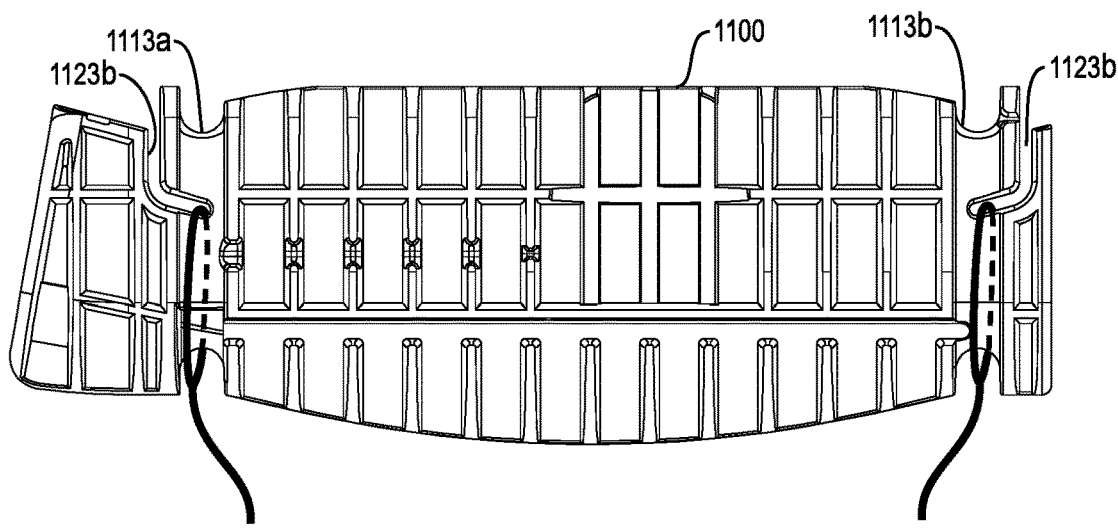
FIG. 13A illustrates an adjustable loop construct assembled to the reduction bar in a reducing configuration, in accordance with this disclosure.
Figure 13B:
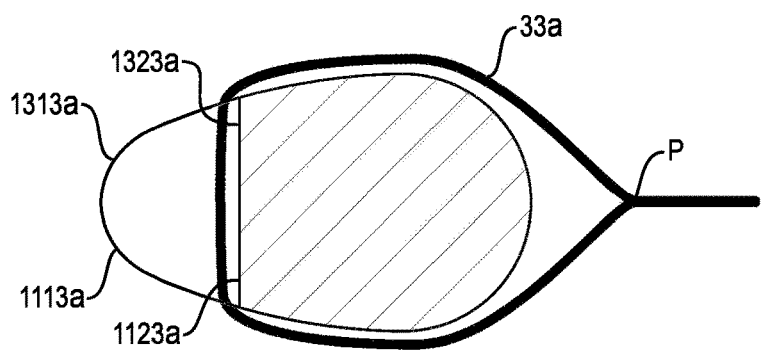
FIG. 13B illustrates a cross section of a reduction bar spool, assembled to a loop of the adjustable loop construct limb, in accordance with this disclosure.
Figure 13C:
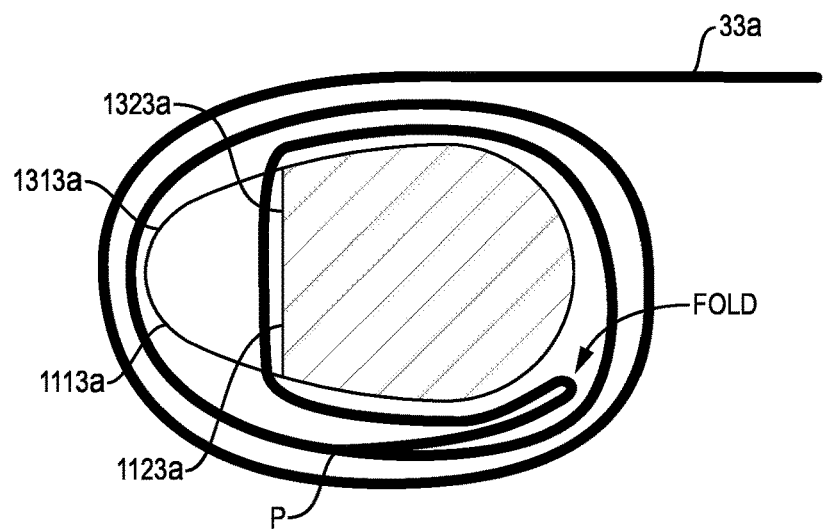
FIG. 13C illustrates the looped end of the adjustable loop construct limb wrapped around the cross section of a reduction bar spool, in accordance with this disclosure.
Figure 13D:
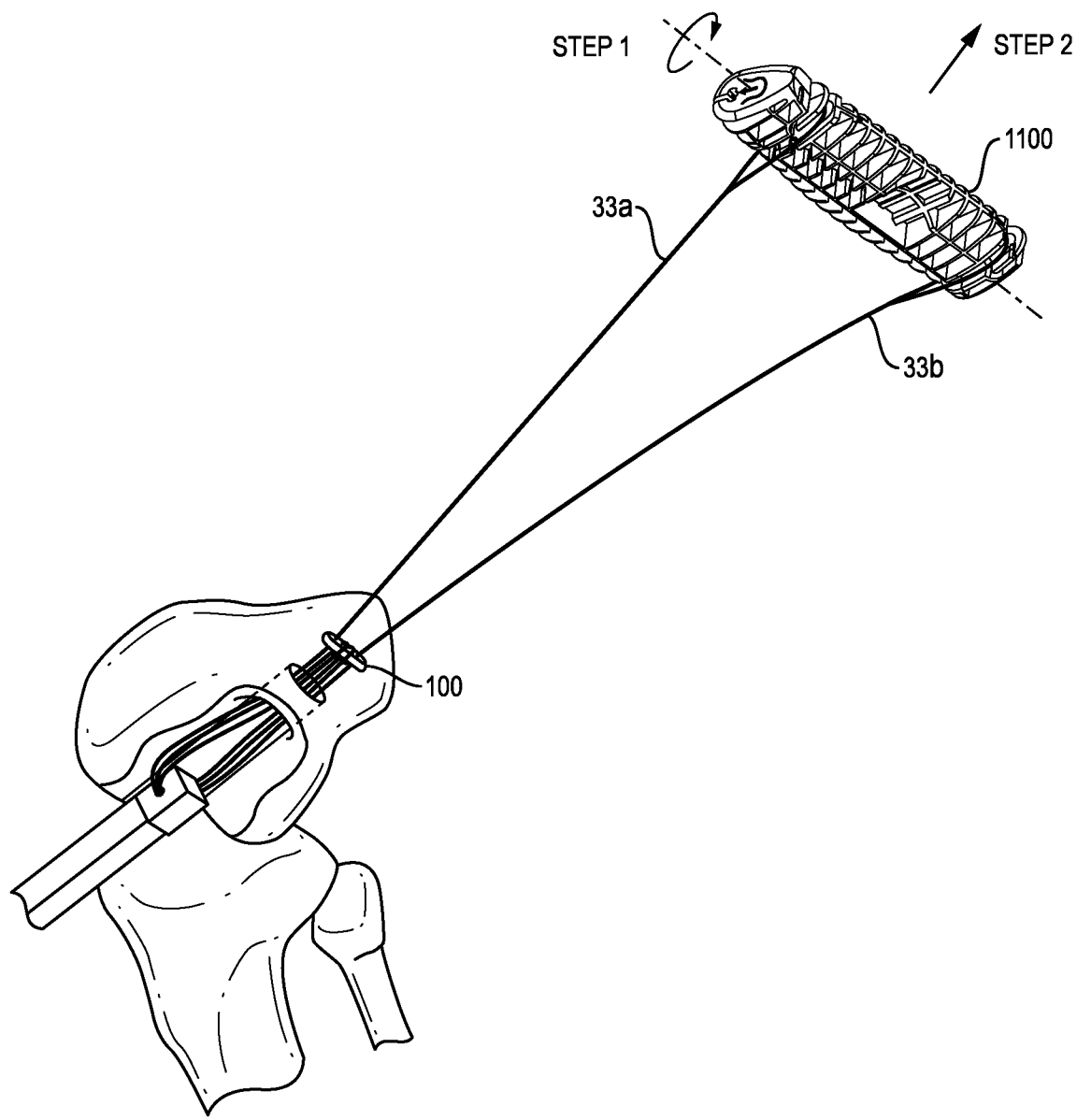
FIG. 13D illustrates a method of reducing a length of the adjustable loop construct limbs (step 1) and also the adjustable loop construct perimeter (step 2) in accordance with this disclosure.

Illustrated in FIGS. 13B and 13C, is a cross section of spool 1113a, illustrating the outermost circumferential surface 1313a and a second surface 1323a defined by notch 1123a (only one spool shown, spools may be similar). Spool 1113b may have the same cross section. Second surface 1323a may define a planar surface 1313a that traverses the reduction bar 1100. Second surface 1323a may define a "short cut" that is configured to inhibit the looped ends 33a, 33b from slipping around the spool 1113a as the bar is rotated (step 1). Each looped ends 33a, 33b may be formed with a spice or knot at point "P". Second surface 1323a may define a corner or discontinuity sufficient to limit the looped end from spinning around the spool out circumference 1313a, such that the looped end 33a may preferentially fold over itself (as illustrated in FIG. 13C) and wrap, without slipping as the bar 1100 is rotated (step 1). Each notch 1123a, 1123b is configured to place a looped end (33a, 33b) within a segment of its respective spool to inhibit slipping or sliding of the looped end 33a, 33b as they are wrap around the corresponding spool 1113a, 1113b. Notch (1123a, 1123b) is configured to form a folded portion of the looped end as the bar 1100 is rotated about the longitudinal axis X-X.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A cortical button configured to be passed through a bone tunnel in an elongate orientation before being flipped to a deployed configuration, the cortical button comprising:
   an oblong body, having a length greater than a width, and a longitudinal axis;
   the width extending from a first sidewall to a second sidewall of the body, the first and second sidewalls along the longitudinal axis between a first and a second end, the body also having a lower surface configured to engage an external bone surface when the cortical button is in the deployed configuration; and a pair of slotted apertures extending through an entire thickness of the body and also extending through the first or second sidewall of the body, defining slotted aperture lateral openings, the slotted aperture lateral openings configured to receive a loop of a flexible strand therethrough;

a pair of enclosed apertures, adjacent the pair of slotted apertures; and a rib extending from the oblong body lower surface and disposed between both the pair of slotted apertures and the pair of enclosed apertures, the rib coextensive along the longitudinal axis with both the pair of slotted and enclosed apertures.

2. The cortical button of claim 1 further comprising a first end aperture disposed between the pair of slotted apertures and the first end, and a second end aperture disposed between the pair of enclosed apertures and the second end.

3. The cortical button of claim 2 wherein the first and second end apertures are axially separated from the rib.

4. The cortical button of claim 1 wherein the rib is an oblong solid body.

5. The cortical button of claim 1 wherein the rib is an oblong body having a longitudinal axis coincident with and parallel to the cortical button longitudinal axis.

6. The cortical button of claim 1 wherein the pair of slotted apertures each define medial surfaces that extend through the cortical button thickness and extend directly from lateral side surfaces of the rib.

7. The cortical button of claim 1 wherein the rib is configured to compensate for a reduced structural integrity of the cortical button, the reduced structural integrity a result of the slotted aperture lateral openings.

8. The cortical button of claim 1 wherein the rib extends perpendicularly less than 2 mm from the oblong body lower surface.

9. The cortical button of claim 1 wherein the rib extends from the oblong body lower surface a distance that is less than the body thickness.

10. A cortical button comprising:

an oblong body, having a length greater than a width, and a longitudinal axis;

the width extending from a first sidewall to a second sidewall of the body, the first and second sidewalls extending along the longitudinal axis between a first and a second end, the oblong body also having a lower surface configured to engage an external bone surface when the cortical button is in the deployed configuration; and a pair of slotted apertures extending through an entire thickness of the body and also extending through one of the first or second sidewall, such that each of the pair of slotted apertures define a lateral opening for receiving a loop of a flexible strand therethrough;

a pair of enclosed apertures, adjacent the pair of slotted apertures; and a rib extending from the lower surface and disposed between the pair of slotted apertures and the pair of enclosed apertures and coextensive along the longitudinal axis with both the pair of slotted apertures and the pair of enclosed apertures, the oblong body width defining a minimum diameter of a bone tunnel through which the cortical button is configured to pass, the rib configured to increase the structural integrity of the cortical button while preserving the minimum diameter.

11. The cortical button of claim 10 wherein the rib is configured to increase the structural integrity and compensate for loss of structural integrity due to the lateral openings.

12. The cortical button of claim 10 wherein the rib is coextensive along the longitudinal axis with the lateral openings.

13. The cortical button of claim 10 further comprising a first end aperture and a second end aperture, both axially separated from the rib.

14. The cortical button of claim 10 wherein the rib is an oblong solid body.

15. The cortical button of claim 10 wherein the rib is an oblong body having a longitudinal axis coincident with and parallel to the cortical button longitudinal axis.

16. The cortical button of claim 10 wherein the pair of slotted apertures each define medial surfaces that extend through the cortical button thickness and are continuous with outer lateral side surfaces of the rib.

17. The cortical button of claim 10 wherein the rib extends perpendicularly from the lower surface, less than 2 mm.

18. The cortical button of claim 10 wherein the rib extends from the lower surface distance that is less than the oblong body width.

* * * * *